United States Patent [19]

Herbig et al.

[11] Patent Number: 5,358,502
[45] Date of Patent: Oct. 25, 1994

[54] PH-TRIGGERED OSMOTIC BURSTING DELIVERY DEVICES

[75] Inventors: Scott M. Herbig; Kelly L. Smith, both of Groton, Conn.

[73] Assignee: Pfizer Inc, New York, N.Y.

[21] Appl. No.: 23,227

[22] Filed: Feb. 25, 1993

[51] Int. Cl.$^5$ ............................................. A61K 9/22
[52] U.S. Cl. .................................. 604/892.1; 424/453
[58] Field of Search .................. 604/892.1; 424/453, 424/468, 471–474, 462, 463, 482

[56] References Cited

U.S. PATENT DOCUMENTS

| | | |
|---|---|---|
| 3,247,066 | 4/1966 | Milosovich, Jr. . |
| 3,952,741 | 4/1976 | Baker . |
| 4,016,880 | 2/1983 | Theeuwes et al. . |
| 4,096,238 | 6/1978 | Zaffaroni et al. . |
| 4,177,256 | 12/1979 | Michaels et al. . |
| 4,503,030 | 3/1985 | Edgren et al. ............... 604/892.1 |
| 4,522,625 | 6/1985 | Edgren . |
| 4,539,199 | 9/1985 | Orbán et al. ................ 525/359.2 |
| 4,578,075 | 3/1986 | Urquhart et al. ............ 604/892.1 |
| 4,587,117 | 5/1986 | Edgren et al. . |
| 4,627,851 | 12/1986 | Wong et al. . |
| 4,681,583 | 7/1987 | Urquhart et al. . |
| 4,693,895 | 9/1987 | Wong et al. ................ 424/473 |
| 4,705,515 | 11/1987 | Wong et al. . |
| 4,830,855 | 5/1989 | Stewart ................ 424/448 |
| 4,851,231 | 7/1989 | Urquhart et al. ............ 424/469 |
| 4,904,474 | 2/1990 | Theeuwes et al. .......... 424/424 |
| 4,910,021 | 3/1990 | Davis et al. ............ 424/456 |

FOREIGN PATENT DOCUMENTS 9001329 2/1990 World Int. Prop. O. .

OTHER PUBLICATIONS

Baker, R. W., John Wiley and Son, "Controlled Release of Biologically Active Agents" pp. 132–155 (1987).
Smith, K. L., Herbig, S. M., Ho, W. S. W., and K. K. Sirkar eds., Van Nostrand Reinhold, "Controlled Release", Membrane Handbook, pp. 915–935 (1992).

Primary Examiner—C. Fred Rosenbaum
Assistant Examiner—V. Alexander
Attorney, Agent, or Firm—Peter C. Richardson; Gregg C. Benson; A. Dean Olson

[57] ABSTRACT

An osmotic bursting device for dispensing a beneficial agent to an aqueous environment. The device comprises a beneficial agent and osmagent surrounded at least in part by a semipermeable membrane. Alternatively the beneficial agent may also function as the osmagent. The semipermeable membrane is permeable to water and substantially impermeable to the beneficial agent and osmagent. A trigger means is attached to the semipermeable membrane (e.g., joins two capsule halves). The trigger means is activated by a pH of from 3 to 9 and triggers the eventual, but sudden, delivery of the beneficial agent. These devices enable the pH-triggered release of the beneficial agent core as a bolus by osmotic bursting.

14 Claims, 10 Drawing Sheets

PH-TRIGGERED OSMOTIC BURSTING DELIVERY DEVICES

BACKGROUND OF THE INVENTION

This invention relates to devices useful for the delivery of a beneficial agent to an environment of use.

In an osmotic device water is imbibed into the device across a semi-permeable membrane due to a lower concentration of water in the device core than in the environment of use. This creates a positive hydrostatic pressure in the device core resulting in release of the beneficial agent contained in the core. Most osmotic delivery systems provide sustained delivery of a beneficial agent (e.g., Baker, R. W., 1987, Controlled Release of Biologically Active Agents John Wiley & Sons pp 132–155; and Smith, K. L. and Herbig, S. M., 1992 "Controlled Release" in Membrane Handbook Ho, W. S. W., and Sirkar, K. K., eds., Van Nostrand Reinhold, pp 915–935).

Osmotic devices have also been developed that release the beneficial agent as a bolus (osmotic bursting systems) (e.g. U.S. Pat. Nos. 3,247,066; 3,952,741; 4,016,880; and 4,177,256). The release of the beneficial agents is initiated once the delivery device is immersed in aqueous solutions.

In an alternative method of delivery of beneficial agents, devices have been developed that dissolve at a specific pH in order to release the agent. Release of the beneficial agent from these formulations is caused by the dissolution of the enteric coating and the subsequent dissolution and/or diffusion of the core components into a receptor solution. Materials that dissolve due to specific pH are commonly used in the pharmaceutical industry as coatings for tablets, particles and capsules. The use of pH-sensitive materials as coatings is described in most reference books describing pharmaceutical formulations.

Typically pH-sensitive materials have been used as coatings to protect labile beneficial agents, or to encapsulate irritating beneficial agents during transit through the stomach, and then release the beneficial agent shortly after entering the small intestine. These coatings have been modified to achieve longer time lags prior to release so that the beneficial agent can be released in the lower end of the small intestine or in the colon. However, these coatings function similarly as common enteric coatings. pH-sensitive coatings that achieve delivery in the colon have been described in patents such as U.S. Pat. No. 4,910,021 and WO 9001329. U.S. Pat. No. 4,910,021 describes using pH-sensitive material to coat a capsule and WO 9001329 describes pH-sensitive coatings on beads containing acid. The acid in the bead core prolongs dissolution of the pH-sensitive coating.

The use of pH-sensitive materials alone to achieve site-specific delivery is difficult because of the problem of leaking beneficial agent prior to the release site or desired delivery time. Typically 10% to 30% of the total beneficial agent is released prematurely. In addition, it is difficult to achieve long time lags before release of the active ingredient after exposure to high pH (because of rapid dissolution or degradation of the pH-sensitive materials).

There are also hybrid systems which combine pH-sensitive materials and osmotic delivery systems. These devices provide for delayed initiation of sustained-release of the beneficial agent. In one device a pH-sensitive matrix or coating dissolves releasing osmotic devices that provide sustained release of the beneficial agent (U.S. Pat. Nos. 4,578,075; 4,681,583; and 4,851,231). A second device consists of a semipermeable coating made of a polymer blend of insoluble and pH-sensitive material. As the pH increases, the permeability of the coating increases, increasing the rate of release of beneficial agent (U.S. Pat. Nos. 4,096,238; 4,503,030; 4,522,625; and 4,587,117).

Another system consists of a "push-pull" osmotic device with a pH-sensitive barrier inside of the semipermeable coating. The pH-sensitive barrier delays sustained osmotic delivery until it is dissolved in high pH solution (U.S. Pat. No. 4,904,474). In yet another system the device has a trilaminate coating consisting of a semipermeable coating, a fatty acid salt or osmotic solute coating, and an outer enteric coating. Due to dissolution of the outer enteric layer, sustained osmotic delivery of the beneficial agent is initiated after exposure to high pH solutions (U.S. Pat. Nos. 4,627,851; 4,693,895; and 4,705,515).

The four above-described osmotic devices with pH-sensitive coatings provide for sustained release of beneficial agent through a drug delivery port by osmotic pumping. The key to the operation of these osmotic systems is an increase in coating permeability as the pH-sensitive coatings dissolve. The release kinetics are affected by the pH-sensitive material either by controlling the time and/or location of delivery or the rate of delivery.

Although the above devices make a significant advance in the field of osmotic delivery devices there is a continuing search for alternative osmotic delivery devices.

SUMMARY OF THE INVENTION

The invention is directed to an osmotic bursting delivery device for dispensing a beneficial agent to an aqueous environment. The device comprises a beneficial agent and osmagent (the beneficial agent may also be the osmagent) surrounded at least in part by a semipermeable membrane. The semipermeable membrane is permeable to water and substantially impermeable to the beneficial agent and osmagent. A trigger means is attached to the semipermeable membrane. The trigger means is activated by a pH of from 3 to 9 and triggers the eventual, but sudden, delivery of the beneficial agent.

These devices enable the pH-triggered release of the beneficial agent core as a bolus (e.g., core) by osmotic bursting. In addition, these devices enable the control of the time lag prior to delivery providing for site-specific delivery of the beneficial agent.

Other objects, features and advantages of the invention will be more apparent to those skilled in the art from the following detailed specification, taken in conjunction with the figures and the accompanying claims.

DETAILED DESCRIPTION OF THE INVENTION

Figure 1:
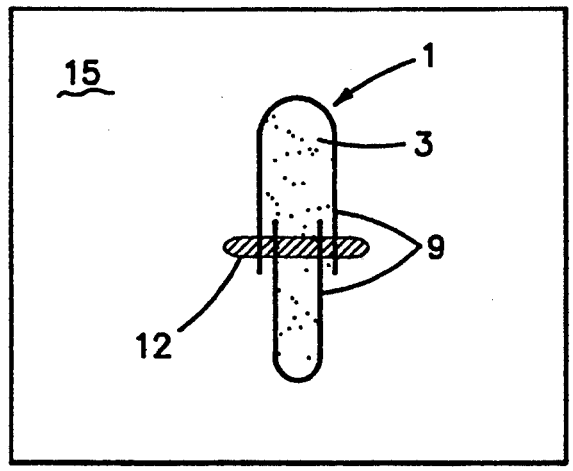
FIG. 1 is a cross-sectional view of an exemplary capsule of this invention.

Any semipermeable membrane (membrane means) that provides sufficient structural support and provides for the diffusion of the aqueous medium into the core while inhibiting the release of the beneficial agent prior to the bursting of the device may be used. By semipermeable is meant that the permeability of the membrane to water is at least five times greater than the permeability of the semipermeable membrane to the beneficial agent, osmagent and other excipients. By aqueous medium is meant a composition containing water as the principal liquid component (e.g., physiological fluids, solutions of organic or inorganic substances particularly electrolytes and mixtures of substance in water). Although, typically the semipermeable membrane totally surrounds the beneficial agent, the semipermeable membrane may be combined with an impermeable wall portion to totally surround the beneficial agent if desired. The semipermeable membrane material has a combination of thickness and material strength so that once the desired hydrostatic pressure has been generated (due to diffusion of water into the device) within the core, the membrane is disrupted thus releasing the beneficial agent. Preferably the membrane is 1 $\mu$m to 1 mm in thickness. Preferably the membrane is 10 $\mu$m to 300 $\mu$m in thickness for human health applications. The semipermeable membrane may be a dense film, a composite, asymmetric in structure, microporous, etc. Since the membrane must remain semipermeable, high-void-volume microporous membranes preferably have skins or dense layers typical of asymmetric membranes or are impermeable to liquid water, but are permeable to water in the gas phase. For microporous membranes typically the total porosity (i.e., void volume) may vary from 20% to 95%. Preferably the maximum pore size is 0.01 $\mu$m to 100 $\mu$m in diameter.

Preferably the semipermeable membrane is composed of polymers or waxes, although appropriately treated inorganic materials such as ceramics, metals or glasses may be used. The following is a preferred listing of semipermeable membrane polymers. The polymer's molecular weight should be such that the polymer is solid at the temperature of use and appropriate for the application (e.g., pharmaceutically acceptable).

Cellulose esters such as cellulose acetate, cellulose acetate acetoacetate, cellulose acetate benzoate, cellulose acetate butylsulfonate, cellulose acetate butyrate, cellulose acetate butyrate sulfate, cellulose acetate butyrate valerate. cellulose acetate caprate, cellulose acetate caproate, cellulose acetate caprylate, cellulose acetate carboxymethoxypropionate, cellulose acetate chloroacetate, cellulose acetate dimethaminoacetate, cellulose acetate dimethylaminoacetate, cellulose acetate dimethylsulfamate, cellulose acetate dipalmitate, cellulose acetate dipropylsulfamate, cellulose acetate ethoxyacetate, cellulose acetate ethyl carbamate, cellulose acetate ethyl carbonate, cellulose acetate ethyl oxalate. cellulose acetate furoate, cellulose acetate heptanoate, cellulose acetate heptylate, cellulose acetate isobutyrate, cellulose acetate laurate, cellulose acetate methacrylate, cellulose acetate methoxyacetate, cellulose acetate methylcarbamate, cellulose acetate methylsulfonate, cellulose acetate myristate, cellulose acetate octanoate, cellulose acetate palmitate, cellulose acetate phthalate, cellulose acetate propionate, cellulose acetate propionate sulfate, cellulose acetate propionate valerate, cellulose acetate p-toluene sulfonate, cellulose acetate succinate, cellulose acetate sulfate, cellulose acetate trimellitate, cellulose acetate tripropionate, cellulose acetate valerate, cellulose benzoate, cellulose butyrate napthylate, cellulose butyrate, cellulose chlorobenzoate, cellulose cyanoacetates, cellulose dicaprylate, cellulose dioctanoate, cellulose dipentanate, cellulose dipentanlate, cellulose formate, cellulose methacrylates, cellulose methoxybenzoate, cellulose nitrate, cellulose nitrobenzoate, cellulose phosphate (sodium salt), cellulose phosphinates, cellulose phosphites, cellulose phosphonates, cellulose propionate, cellulose propionate crotonate, cellulose propionate isobutyrate, cellulose propionate succinate, cellulose stearate, cellulose sulfate (sodium salt), cellulose triacetate, cellulose tricaprylate, cellulose triformate, cellulose triheptanoate, cellulose triheptylate, cellulose trilaurate, cellulose trimyristate, cellulose trinitrate, cellulose trioctanoate, cellulose tripalmitate, cellulose tripropionate, cellulose trisuccinate, cellulose trivalerate, cellulose valerate palmitate.

Cellulose ethers such as 2-cyanoethyl cellulose, 2-hydroxybutyl methyl cellulose, 2-hydroxyethyl cellulose, 2-hydroxyethyl ethyl cellulose, 2-hydroxyethyl methyl cellulose, 2-hydroxypropyl cellulose, 2-hydroxypropyl methyl cellulose, dimethoxyethyl cellulose acetate, ethyl 2-hydroxylethyl cellulose, ethyl cellulose, ethyl cellulose sulfate, ethylcellulose dimethylsulfamate, methyl cellulose, methyl cellulose acetate, methylcyanoethyl cellulose, sodium carboxymethyl 2-hydroxyethyl cellulose, sodium carboxymethyl cellulose.

Polysulfones such as polyethersulfones.
Polycarbonates.
Polyurethanes.
Polyvinyl acetates.
Polyvinyl alcohols.
Polyesters.

Polyalkenes such as polyethylene, ethylene vinyl alcohol copolymer, polypropylene, poly(1,2-dimethyl-1-butenylene), poly(1-bromo-1-butenylene), poly(1, butene), poly(1-chloro-1-butenylene), poly(1-decyl-1-butenylene), poly(1-hexane), poly(1-isopropyl-1-butenylene), poly(1-pentene), poly(3-vinylpyrene), poly(4-methoxyl 1-butenylene); poly(ethylene-co-methyl styrene), poly vinyl-chloride, poly(ethylene-co-tetrafluoroethylene), poly(ethylene-terephthalate), poly(dodecafluorobutoxylethylene), poly(hexafluoroprolylene), poly(hexyloxyethylene), poly(isobutene), poly(isobutene-co-isoprene), poly(isoprene), polybutadiene, poly[(pentafluoroethyl)ethylene], poly[2-ethylhexyloxy)ethylene], poly(butylethylene), poly(tertbutylethylene), poly(cylclohexylethylene), poly[(-cyclohexylmethyl)ethylene], poly(cyclopentylethylene), poly(decylethylene), poly(dodecylethylene), poly(neopentylethylene), poly(propylethylene).

Polystyrenes such as poly(2,4-dimethyl styrene), poly(3-methyl styrene), poly(4-methoxystyrene), poly(4-methoxystyrene-stat-styrene), poly(4-methyl styrene), poly(isopentyl styrene), poly(isopropyl styrene).

Polyvinyl esters or polyvinyl ethers such as poly(benzoylethylene), poly(butoxyethylene), poly(chloroprene), poly(cyclohexloxyethylene), poly(decyloxyethylene), poly(dichloroethylene), poly(difluoroethylene), poly(vinyl acetate), poly(vinyltrimethyilstyrene).

Polysiloxanes such as poly(dimethylsiloxane).

Polyacrylic acid derivatives such as polyacrylates, polymethyl methacrylate, poly(acrylic acid) higher alkyl esters, poly(ethylmethacrylate), poly(hexadecyl methacrylate-co-methylmethacrylate), poly(methylacrylate-co-styrene), poly(n-butyl methacrylate), poly(n-butyl-acrylate), poly(cyclododecyl acrylate), poly(benzyl acrylate), poly(butylacrylate), poly(secbutylacrylate), poly(hexyl acrylate), poly(octyl acrylate), poly(decyl acrylate), poly(dodecyl acrylate), poly(2-methyl butyl acrylate), poly(adamantyl methacrylate), poly(benzyl methacrylate), poly(butyl methacrylate), poly(2-ethylhexyl methacrylate), poly(octyl methacrylate), acrylic resins.

Polyamides such as poly(iminoadipoyliminododecamethylene), poly(iminoadipoyliminohexamethylene).

Polyethers such as poly(octyloxyethylene), poly(oxyphenylethylene), poly(oxypropylene), poly(pentyloxyethylene), poly(phenoxy styrene), poly(secbutroxylethylene), poly(tert-butoxyethylene).

Exemplary membrane waxes include: insect and animal waxes such as chinese insect wax, beeswax, spermaceti, fats and wool wax; vegetable waxes such as bamboo leaf wax, candelilla wax, carnauba wax, Japan wax, ouricury wax, Jojoba wax, bayberry wax, Douglas-Fir wax, cotton wax, cranberry wax, cape berry wax, ricebran wax, castor wax, indian corn wax, hydrogenated vegetable oils (e.g., castor, palm, cottonseed, soybean), sorghum grain wax, Spanish moss wax, sugarcane wax, caranda wax, bleached wax, Esparto wax, flax wax, Madagascar wax, orange peel wax, shellac wax, sisal hemp wax and rice wax; mineral waxes such as Montan wax, peat waxes, petroleum wax, petroleum ceresin, ozokerite wax, microcrystalline wax and paraffins; and synthetic waxes such as polyethylene wax, Fischer-Tropsch wax, chemically modified hydrocarbon waxes and cetyl esters wax.

Especially preferred semipermeable membranes include: cellulose esters and cellulose ethers; polyacrylic acid derivatives such as polyacrylates and polyacrylate esters; and polyvinyl alcohols and polyalkenes such as ethylene vinyl alcohol copolymer.

Any material and structural form may be used as the pH-sensitive trigger means that maintains the integrity of the device until triggered by a solution of the desired pH. The pH-sensitive trigger means may be for example a porous or dense coating. Preferably, the trigger means provides sufficient structural support to inhibit the hydrostatic pressure in the core from bursting, or disrupting the semipermeable membrane and releasing the beneficial agent until triggered. Typically, the trigger pH is between about 3 to 9 although in some applications it may be higher or lower. Preferably, the trigger pH is from about 6.5 to about 8.5 for human health applications. The trigger pH is the threshold pH value or range of values at which either above or below the trigger pH the pH-sensitive material degrades, and/or dissolves. Thus, devices can be made that are stable in solutions and then as the pH rises above the trigger pH are activated. Likewise, devices can be made that are stable in solutions and then as the pH drops below the trigger pH are activated. Once activated, the beneficial agent is released after the desired time lag.

In one embodiment a pH-sensitive trigger means is used that is capable of becoming more permeable to water and/or losing physical strength following triggering by a solution of the desired pH (either above or below the trigger pH). The increase in permeability allows the hydrostatic pressure inside the core to more rapidly increase, until the semipermeable membrane bursts (the major contribution of increased permeability is to shorten the time lag prior to bursting).

In another embodiment a pH-sensitive trigger means is used to hold together two capsule portions. The trigger means is capable of losing its adhesive quality or strength (e.g., degrades) following triggering by a solution of the desired pH (either above or below the trigger pH). The reduction in adhesion strength allows the hydrostatic pressure inside the core to push apart the capsule portions held together by the adhesive trigger means, thus releasing the contents.

Thus the pH-sensitive trigger means is attached (e.g., bonded, encasing, friction fit, partially encasing) to the semipermeable membrane, for example, either as an adhesive, joining portions of the semipermeable membrane, or as an outer coating. The failing of the pH-sensitive means causes water to be imbibed into the device (via osmotic pressure) more rapidly with a resultant increase in hydrostatic pressure and the resultant bursting of the device followed by release of beneficial agent. In addition, the failing of the pH-sensitive means weakens the device sufficiently such that the hydrostatic pressure inside the device bursts the device, and the contents are released. Significantly, this differentiates these devices from osmotic devices where the active agent is released over a considerable time frame. In these devices the active agent is released as a bolus. The pH-sensitive trigger means is preferably 1 $\mu$m to 1 mm in thickness. Preferably a pH-sensitive adhesive is from 10 $\mu$m to 500 $\mu$m thick and a pH-sensitive coating is from 10 $\mu$m to 300 $\mu$m thick.

Typically the pH-sensitive materials are insoluble solids in neutral or acidic aqueous solutions, and then they dissolve (or degrade and dissolve) as the pH of the solution rises above a pH value ranging from 3 to 9, preferably 6 to 8. Exemplary pH-sensitive materials include polyacrylamides, phthalate derivatives (i.e., compounds with covalently attached phthalate moieties) such as acid phthalates of carbohydrates, amylose acetate phthalate, cellulose acetate phthalate, other cellulose ester phthalates, cellulose ether phthalates, hydroxy propyl cellulose phthalate, hydroxypropyl ethylcellulose phthalate, hydroxypropyl methyl cellulose phthalate, methyl cellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinyl acetate phthalate copolymer, styrene and maleic acid copolymers, formalized gelatin, gluten, shellac, salol, keratin, keratin sandarac-tolu, ammoniated shellac, benzophenyl salicylate, cellulose acetate trimellitate, cellulose acetate blended with shellac, hydroxypropylmethyl cellulose acetate succinate, oxidized cellulose, polyacrylic acid derivatives such as acrylic acid and acrylic ester copolymers, methacrylic acid and esters thereof, vinyl acetate and crotonic acid copolymers.

Preferred pH-sensitive materials include shellac; phthalate derivatives, particularly cellulose acetate phthalate, polyvinyl acetate phthalate and hydroxypropyl methylcellulose phthalate; polyacrylic acid derivatives, particularly polymethyl methacrylate blended with acrylic acid and acrylic ester copolymers; and vinyl acetate and crotonic acid copolymers.

Preferably the pH-sensitive material is blended with an inert non-dissolving material. By inert is meant a material that is not substantially affected by a change in pH in the triggering range. By altering the proportion of a pH-sensitive material to inert non-dissolving material the time lag subsequent to triggering and prior to release may be tailored. For example, for capsule devices, the blend of pH-sensitive material to inert non-dissolving material may be tailored to control the time when the capsule halves separate after being triggered. Thus, preferably a proportional mixture of pH-sensitive material to inert nondissolving material is used that provides the desired release time lag subsequent to triggering. Any inert non-dissolving material may be used that does not react with the trigger. Typically, increasing the proportion of inert nondissolving material will lengthen the time lag after triggering and subsequent to release of the beneficial agent. Preferably, the inert material is selected from the list of materials given for the semipermeable membrane (above).

Alternatively pH-sensitive materials can be used that are insoluble solids in neutral or alkaline solutions, and then they dissolve (or degrade and dissolve) as the pH of the solution drops below a pH value ranging from 3 to 9. Exemplary pH-sensitive materials include copolymers of acrylate polymers with amino substituents and acrylic acid esters. Additional pH-sensitive materials include polyfunctional polymers containing multiple groups that become ionized as the pH drops below their pKa. A sufficient quantity of these ionizable groups must be incorporated in the polymer such that in aqueous solutions having a pH below the pKa of the ionizable groups, the polymer dissolves. These ionizable groups can be incorporated into polymers as block copolymers, or can be pendent groups attached to a polymer backbone, or can be a portion of a material used to crosslink or connect polymer chains. Examples of such ionizable groups include polyphosphene, vinyl pyridine, vinyl aniline, polylysine, polyornithine, other proteins, and polymers with substituents containing amino moieties.

The semipermeable membrane surrounds at least part of the device core. The device core contains the beneficial agent. If the beneficial agent is not an osmagent then the core must also contain an osmagent. The osmagent may be any material that increases the osmotic pressure of the core, thus, increasing the hydrostatic pressure inside the semipermeable membrane to achieve the desired membrane disruption. The core must have an effective osmotic pressure greater than that of the surrounding fluid in the environment of use (e.g., 7 atm in humans) so that there is a net driving force for water to enter the core. The osmagent can be either soluble or swellable. Examples of osmotically effective solutes are inorganic and organic salts and sugars. Osmotically effective compounds may be used singly or in combination and include magnesium sulfate, magnesium chloride, sodium chloride, lithium chloride, potassium sulfate, sodium carbonate, sodium sulfite, lithium sulfate, potassium chloride, calcium carbonate, sodium sulfate, calcium sulfate, potassium acid phosphate, calcium lactate, d-mannitol, urea, inositol, magnesium succinate, tartaric acid, water soluble acids, alcohols, surfactants, and carbohydrates such as raffinose, sucrose, glucose, lactose, fructose, algin, sodium alginate, potassium alginate, carrageenan, fucoridan, furcellaran, laminaran, hypnea, gum arabic, gum ghatti, gum karaya, locust bean gum, pectin and starch. For the devices of this invention which are to be employed to deliver a drug to humans or animals, any such solute should be pharmaceutically acceptable. A preferred device comprising such a solute contains a range of 15 to 95% osmotically effective solute (e.g., osmagent or beneficial agent that is an osmagent).

Typically for those devices that are capsules sealed with a pH-sensitive material a water-swellable component such as a hydrogel is used. The swellable excipient aids in forcing the capsule off of the capsule body, once the device is triggered. For analogous reasons swellable components are typically added to tablets and beads. Exemplary hydrogels include polyacrylic acid derivatives (e.g., polyacrylates, poly- methyl methacrylate, poly(acrylic acid) higher alkyl esters, poly(ethylmethacrylate), poly(hexadecyl methacrylate-co-methylmethacrylate), poly(methylacrylate-co-styrene), poly(n-butyl methacrylate), poly(n-butyl-acrylate), poly(cyclododecyl acrylate), poly(benzyl acrylate), poly(butylacrylate), poly(secbutylacrylate), poly(hexyl acrylate), poly(octyl acrylate), poly(decyl acrylate), poly(dodecyl acrylate), poly(2-methyl butyl acrylate), poly(adamantyl methacrylate), poly(benzyl methacrylate), poly(butyl methacrylate), poly(2-ethylhexyl methacrylate), poly(octyl methacrylate), acrylic resins), polyacrylamides, poly(hydroxy ethyl methacrylate), poly(vinyl alcohol), poly(ethylene oxide), poly N-vinyl-2-pyrrolidone, naturally occurring resins such as polysaccharides (e.g., dextrans, water-soluble gums, starches, chemically modified starches), cellulose derivatives (e.g., cellulose esters, cellulose ethers, chemically modified cellulose, microcrystalline cellulose, sodium carboxymethylcellulose and methylcellulose). Preferred hydrogels include ethylene oxide derivatives such as polyethylene oxide (PEO) because of its relatively large capacity to absorb water and swell, its availability in a variety of different molecular weights in commercial quantities, its biocompatibility, and its safety and favorable toxicity properties. PEO is commercially available and can be obtained having a variety of different molecular weights. Other preferred hydrogels are starches.

The hydrogel employed can be a blend of, for example, two or more polymers. For example, different hydrogels comprising blends of PEO polymers of different molecular weights can be prepared and employed. Such blends can be adjusted to assist in achieving the desired delivery rates for the beneficial agents.

The beneficial agents used in the devices of this invention include for example, any physiologically or pharmacologically active substance that produces a localized or systemic effect in animals including mammals (e.g., human beings).

Examples of active substances include inorganic and organic compounds such as drugs that act on the peripheral nerves, adrenergic receptors, cholinergic receptors, nervous system, skeletal muscles, cardiovascular smooth muscles, blood circulatory system, synaptic sites, neuroeffector junctional sites, endocrine and hormone systems, immunological system, reproductive system, autacoid systems, alimentary and excretory systems, inhibitors of autocolds, and histamine systems. The pharmaceutical agent that can be delivered for acting on these systems includes antidepressants, hypnotics, sedatives, psychic energizers, tranquilizers, anticonvulsants, muscle relaxants, antisecretories, anti-parkinson agents, analgesics, anti-inflammatory agents, local anesthetics, muscle contractants, antibiotics, antimicrobials, anthelmintics, anti-malarials, hormonal agents, contraceptives, histamines, antihistamines, adrenergic agents, diuretics, antiscabiotics, anti-pediculars, anti-parasites, anti-neoplastic agents, hypoglycemics, electrolytes, vitamins, diagnostic agents and cardiovascular pharmaceuticals.

Also included in such active substances are prodrugs of the above-described drugs. Such drugs or prodrugs can be in a variety of forms such as the pharmaceutically acceptable salts thereof.

The term beneficial agent is also meant to include other substances for which it is desirable and/or advantageous to control delivery into an environment of use. Examples of such substances include: agrichemicals such as insecticides, herbicides, fertilizers, fungicides, pheromones, algaecides, insect growth regulators, plant growth regulators, reaction catalysts, reaction feedstocks, pH controlling agents, enzymes, enzyme inhibitors, disinfectants, absorbants, flavors and fragrances.

In addition to the above-mentioned ingredients of the devices of this invention, other common pharmaceutical excipients may be present. Examples include viscosity modifiers, antioxidants, stabilizers, pH controlling agents, flavoring agents, binding agents, tablet disintegrants, osmotic agents, lubricants, gildants; adsorbents, inert diluents, etc. Typical examples are: binding agents such as carboxymethyl cellulose, hydroxyethyl cellulose, acacia gum, guar gum, microcrystalline cellulose, starch sodium alginate, polyethylene glycols, corn syrup, sucrose, lactose, mannitol, calcium phosphate and ethyl cellulose; tablet disintegrants such as starch, microcrystalline cellulose, clays and sodium alginate, polyethylene glycols, corn syrup, sucrose, lactose, mannitol, calcium phosphate and ethyl cellulose; tablet disintegrants such as starch, microcrystalline cellulose, clays and sodium alginate; lubricants such as talc, polyethylene glycol, corn starch, sodium benzoate and sodium acetate; gildants such as microfine silicas, corn starch, microcrystalline cellulose and talc; adsorbents such as silicas and starches; inert diluents such as lactose, dextrose, starch, microcrystalline cellulose, calcium phosphate, calcium sulfate, sucrose, mannitol, kaolin and magnesium aluminum sulfate; and osmotic agents and buffering agents such as citric acid, sodium phosphate, glucose, potassium citrate, potassium sorbate, sodium bicarbonate, sodium chloride and sodium citrate.

The devices of this invention can be advantageously tailored by altering time lags between exposure of the device to the trigger and release of the beneficial agent. Thus, for example, preferably a one to ten hour time lag is sufficient to provide release to the duodenum, ileum, jejunum or colon if the device is triggered immediately after leaving the stomach. The time lag can be tailored by controlling the thickness and/or the composition of the pH-trigger means. Thus, preferably the pH-trigger means has a composition such that it provides the desired time lag (e.g., sufficient time lag to provide release to the duodenum, ileum, colon and jejunum). Alternatively, and preferably, the membrane has a thickness such that it provides the desired time lag (e.g., sufficient time lag to provide release to the duodenum, ileum, colon or jejunum) as thinner membranes typically open faster than thicker membranes. The time lag increases with increasing coating thickness or seal thickness, as shown in Examples 7, 11, and 14. In addition, the time lag increases as the content of pH-sensitive material in the pH-trigger means decreases, as shown in Examples 6, 12, 13, and 14. Thus, by controlling the coating thickness and the composition of the pH-trigger means, time lags ranging from less than one hour to greater than 10 hours can easily be achieved (shown in Example 14).

Although any mixture of the above ingredients may be used that satisfactorily delivers the beneficial agent, typically the pH-trigger means is 0.01% to 30% by weight of the device and the membrane including pH-trigger means is typically 1% to 30% of the device. Preferably the pH-trigger means is 0.1% to 20% of the device and the membrane, including pH-trigger means, is 1% to 20% of the device. The amount of beneficial agent is the amount that is sufficient to achieve the desired effect (e.g., therapeutic effect). The remainder weight can be made up of any desired formulation ingredients (described above) and other additives.

The devices of this invention can also be administered within a capsule comprising a water-soluble wall. For example, the devices can be manufactured to be of suitable size for inclusion either singularly or multiply within a gelatin capsule such that when the capsule dissolves the device(s) are released into the environment of use. While the devices to be included within a capsule can be of a variety of shapes, a preferred shape for such devices is spherical or substantially spherical. The exact number and size of such devices can and will be determined according to a variety of well known factors. For example, the environment of use, the beneficial agent or agents, the amount of beneficial agent and the rate of release are all factors to be considered in determining the size, shape, and number of devices to be included in such capsules as well as the composition of the capsule.

The dispensing device shape and dimensions can vary based on the particular application (e.g., tablets, beads or capsules). Common exemplary shapes are spherical cylindrical, tablet-shape, and capsular-shape. The dispensing device dimensions may vary with the desired application (e.g., cattle tablets, human tablets). The shape and size may also vary depending on the application so that for example the tablet is suitable depending on the quantity and rate of beneficial agent delivery which vary based on the application. Preferably, the tablet is 5 to 20 mm in diameter and the beads are 0.1 to 5 mm in diameter. However, typical capsule dimensions range from about 1 cm to about 2.5 cm in length and about 0.3 cm to about 1 cm in diameter for human health applications. For animal applications, such as ruminal delivery to cattle, typical dimensions range from about 5 cm to about 10 cm in length and about 1 cm to about 3 cm in diameter. For other applications, such as agrichemicals, chemical reactions, flavors, and fragrances, shapes and sizes will be determined by the method of use and may be different from those listed above.

Figure 2:
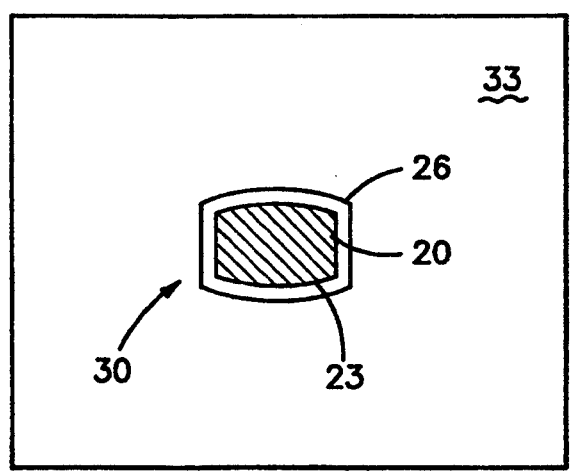
FIG. 2 is a cross-sectional view of an exemplary tablet of this invention.

A clearer understanding of the devices of this invention may be had by reference to FIGS. 1 and 2. In FIG. 1 the beneficial agent 3 and other excipients are surrounded by the semipermeable membrane 9 capsule halves. Joining the semi-permeable membrane 9 capsule halves is a band of pH-sensitive trigger 12. External to the device 1 is the environment of use 15 including the aqueous solution of an appropriate pH. In FIG. 2 the beneficial agent 20 and other excipients are surrounded by a semipermeable membrane 23. Surrounding the semipermeable membrane 23 is the pH-sensitive trigger coating 26. External to the device 30 is the environment of use 33 including the aqueous solution of an appropriate pH.

The devices of this invention having the above described desired characteristics may be made using the above described materials using the following processes and other conventional methods.

Capsule formulations may be prepared by forming a cap and body of the above-described polymers. In a conventional fashion, polymers may be molded into the desired shapes and sintered or dip-coated (in a similar fashion to the way hard gelatin capsules are made). Alternatively, hard gelatin capsules may be coated with the semipermeable coating. These semipermeable capsule bodies and caps are then filled with the beneficial agent and other excipients (e.g., osmagent, swellable component) using standard capsule filling techniques. Then the capsule is sealed with the desired pH-sensitive material and assembled. This may be performed using conventional capsule-sealing equipment.

Tablets may be prepared using conventional processes and conventional tableting and tablet-coating equipment. The tablet cores can be made by direct compression of the beneficial agent and other desired excipients (e.g., osmagent swellable material) or other common tableting methods. To minimize incompatibilities or provide a suitable substrate for the semipermeable coating, the tablets may first be coated with a water-soluble precoat. The precoat may consist of sugars, salts, soluble cellulose derivatives or other water-soluble materials.

The tablet cores are coated with either a dense or microporous semipermeable membrane using conventional coating techniques. Microporous coatings can also be made by a variety of methods, such as phase inversion, scintering, leaching, and irradiation. These films can be applied using conventional equipment such as fluid-bed coaters, pan-coaters, spray-dryers or by dip-coating. Several different phase-inversion methods, such as the vapor quench process, the dry process, the liquid quench process, and the thermal process, can be used to form microporous coatings.

In the vapor quench process, membrane formation is accomplished by penetration of a precipitant for the polymer into the solution film from the vapor phase, which may be saturated with the solvent used. A porous membrane is produced with or without a skin and typically with an even distribution of pores over the membrane thickness.

In the dry process, the polymer is dissolved in a mixture of a solvent and a nonsolvent, of which the solvent is more volatile. The polymer precipitates when the mixture shifts in composition during evaporation to a higher nonsolvent content. A skinned or nonskinned microporous membrane can be the result.

In the liquid quench process, film formation is caused by the immersion of the polymer film in a nonsolvent bath. The polymer precipitates as a result of solvent loss and nonsolvent penetration (exchange of the solvent with non-solvent). A skinned or nonskinned microporous membrane can be the result.

In the thermal process, a solution of polymer in a mixed solvent, which is on the verge of precipitation, is brought to phase separation by a cooling step. A skinned or nonskinned microporous membrane can be the result.

Microporous coatings can also be made by inclusion of a leachable component in the coating formulation. For example, small sugar, salt, or water-soluble polymer particles could be suspended or dissolved in the coating solution. Once the coating is applied, then the water-soluble materials can be leached out by immersion in water, forming a microporous structure.

A second layer or coating of pH-sensitive material is applied over the semipermeable coating on tablets. This coating may be applied using standard coating methods analogous to those described to apply the semipermeable coating.

Beads, granules or multiparticulates may be prepared by analogous methods to those used to prepare tablets.

Preferred devices include those described in Examples 12, 13, and 14 described generally below. Particularly preferred capsules include those having a semipermeable membrane of ethylene vinyl alcohol, cellulose acetate or ethylcellulose surrounding the beneficial agent and containing an aqueous swellable material such as sodium carboxymethylcellulose in the core. The capsule halves are sealed together with a pH-sensitive adhesive consisting of a mixture of polymethylmethacrylate and acrylic acid/acrylic ester copolymer, preferably about 5 to 50 wt. % polymethylmethacrylate and 50 to 75 wt. % acrylic acid/acrylic ester copolymer and particularly about 15 to 25 wt. % polymethylmethacrylate and 75 to 85 wt. % acrylic acid/acrylic ester copolymer. Sufficient pH-sensitive polymer is used to provide a seal thickness of 20 μm to 100 μm.

Particularly preferred tablets include those having a core of beneficial agent, osmagent (preferably lactose), and aqueous swellable material (preferably sodium carboxymethylcellulose). The tablets have a semipermeable membrane of cellulose acetate which is preferably about 20 to 100 μm thick. The semipermeable membrane is surrounded by a pH-sensitive coating made of cellulose acetate phthalate coating blended with from 0 to 75 wt. % cellulose acetate, preferably about 5 to 75 wt. % cellulose acetate and 25 to 95 wt. % cellulose acetate phthalate and particularly about 25 to 35 wt. % cellulose acetate and 65 to 75 wt. % cellulose acetate phthalate. Sufficient pH-sensitive polymer is used to provide a thickness of 20 μm to 150 μm.

Particularly preferred multiparticulate beads are those having the same cores as are described for the tablets (above). Likewise the beads have a cellulose acetate semipermeable coating which is preferably about 15 to 50 μm thick. The semipermeable membrane is coated with a pH-sensitive coating made of cellulose acetate phthalate blended with from 0 to 75 wt. % cellulose acetate, preferably, about 5 to 75 wt. % cellulose acetate and 25 to 95 wt. % cellulose acetate phthalate and particularly about 40 to 60 wt. % cellulose acetate and 40 to 60 wt. % cellulose acetate phthalate. Preferably, sufficient pH-sensitive polymer is used to provide a thickness of 15 μm to 120 μm.

It should be understood that the invention is not limited to the particular embodiments shown and described herein, but that various changes and modifications may be made without departing from the spirit and scope hereof as defined by the following claims.

The following materials were used in the Examples (below).

| | |
|---|---|
| cellulose acetate 398-10 polymer | Eastman Chemical Products, Inc. Kingsport, TN |
| cellulose acetate 398-3 polymer | Eastman Chemical Products, Inc. Kingsport, TN |
| cellulose acetate butyrate 381-20 | Eastman Chemical Products, Inc. Kingsport, TN |
| cellulose acetate phthalate (CAP) polymer | Eastman Chemical Product, Inc. Kingsport, TN |
| cellulose acetate phthalate CD-910 polymer | FMC Corp., New York, NY |
| cellulose acetate trimelitate | Eastman Chemical Product, Inc. Kingsport, TN |
| microcrystalline cellulose Avicel pH101 | FMC Corp., New York, NY |
| sodium carboxymethyl cellulose Ac-Di-Sol | FMC Corp., New York, NY |
| methyl cellulose Methocel E6 premium | Dow Chemical Co., Midland, MI |
| methyl cellulose Methocel E3 premium | Dow Chemical Co., Midland, MI |
| polymethyl methacrylate V-920 | Rohm & Haas, Philadelphia, PA |
| acrylic acid/acrylic ester copolymer Eudragit S-100 | Rohm Pharma., Darmstadt, Germany |
| acryllic acid/acrylic ester copolymer Eudragit L | Rohm Pharma., Darmstadt, Germany |
| acrylic acid/acrylic ester copolymer Eudragit RS | Rohm Pharma. Darmstadt, Germany |
| acrylic acid/acrylic ester copolymer Eudragit RL | Rohm Pharma., Darmstadt, Germany |
| polyvinyl alcohol Elvanol 51-05 | DuPont Co., Wilmington, DE |
| ethylene vinyl alcohol copolymer EVAL-F | Eval Co., of America (Lisle, IL) |
| Nupareils (sucrose beads) | Ingredient Technology Corp. (Pennsauken, NJ) |

EXAMPLE 1

FORMATION OF pH-TRIGGERED MEMBRANE TABLET COATINGS APPLIED BY SPRAY DRYING

A pH-triggered coating solution was made of 1.8 wt. % cellulose acetate 398-10 (Eastman Chemical Products, Inc.) and 4.2 wt. % cellulose acetate phthalate CD-910 (FMC Corp.) dissolved in acetone. The solution was stored in a sealed container at room temperature until used. The trigger-pH is believed to range from 5.5 to 7.5 for the coating described in this example.

Pseudoephedrine tablets made by standard direct-compression techniques and consisting of 14 wt. % pseudoephedrine, 41 wt. % lactose, 40 wt. % Avicel pH101 (FMC Corp.) and 5 wt. % AcDiSol (FMC Corp.) (total weight of 350 mg) were precoated with a solution of 5 wt. % sucrose and 5 wt. % Methocel E6 Premium (Dow Chemical Co.) dissolved in deionized water and applied by spray drying using a STREA-1 (Aeromatic) spray coater (total tablet weight 388 mg). The precoated tablets were then spray coated using the STREA-1 with a solution of 5 wt. % cellulose acetate 398-3 (Eastman Chemical Products, Inc.) dissolved in acetone to form a semipermeable coating (total tablet weight 392.7 mg). Finally, the tablets were spray coated using the STREA-1 with the pH-triggered coating solution described above (total tablet weight 418.1 mg).

Equipment: STREA-1 with plexiglass bowl for precoat, and stainless steel wurster bowl (without pipe support) for semipermeable and pH-triggered coats, 1 mm nozzle, peristaltic pump, balance, and 90 psi house air supply. (Aeromatic, Inc., Columbia, Md.).

| Spray Conditions: | Precoat | Semipermeable | pH-triggered |
|---|---|---|---|
| Sample Size | 28.93 g | 31.74 g | 31.74 g |
| Heater Setting | 97° C. | 52° C. | 52° C. |
| Feed-Solution Spray Rate | 10 g/min | 10 g/min | 10 g/min |
| Atomization Air Pressure | 2.4 bar | 2.2 bar | 2.2 bar |
| Blowback Air Pressure | 0 bar | 0 bar | 0 bar |
| Fluidization Air Rate | 140 m³/hr | 140 m³/hr | 140 m³/hr |

The coatings formed in the manner described above were dense. The 130 μm sucrose/methocel E6 precoat provided a smooth substrate for application of the semipermeable cellulose acetate coating. The semipermeable cellulose acetate coating was about 25 μm thick and prevented the drug from leaking prematurely. The pH-triggered membrane coating was about 100 μm thick and degraded at a predictable rate when triggered by a change in pH. Due to degradation of the pH-sensitive coating, the tablet coating burst and released the tablet contents.

EXAMPLE 2

FORMATION OF pH-TRIGGERED MEMBRANE TABLET COATINGS APPLIED BY SPRAY DRYING

A pH-triggered coating solution was made of 2.25 wt. % polymethyl methacrylate V920 (Rohm Haas), 1.5 wt. % Eudragit S-100 (Rohm Pharma), and 3.75 wt. % citric acid dissolved in acetone. The solution was stored in a sealed container at room temperature until used.

Pseudoephedrine tablets made by standard direct-compression techniques and consisting of 7 wt. % pseudoephedrine, 48 wt. % lactose, 40 wt. % Avicel pH101 (FMC Corp.) and 5 wt. % AcDiSol (FMC Corp.) (total weight of 350 mg) were precoated by spray drying with a solution of 5 wt. % sucrose and 5 wt. % Methocel E3 Premium (Dow Chemical Co.) dissolved in deionized water using a STREA-1 (Aeromatic) spray coater (total tablet weight 426 mg). The precoated tablets were then spray coated using the STREA-1 with a solution of 5 wt. % cellulose acetate butyrate 381-20 (Eastman Chemical Products, Inc.) dissolved in acetone (total tablet weight 516 mg). Finally, the tablets were spray coated using the STREA-1 with the pH-triggered coating solution described above (total tablet weight 603 mg).

Equipment: STREA-1 with plexiglass bowl for precoat, and stainless steel wurster bowl (without pipe support) for semipermeable and pH-triggered coats, 0.8 mm nozzle, peristaltic pump, balance, and 90 psi house air supply.

| Spray Conditions: | Precoat | Semipermeable | pH-triggered |
|---|---|---|---|
| Sample Size | 17.6 g | 10.7 g | 12.6 g |
| Heater Setting | 100° C. | 40° C. | 40° C. |
| Feed-Solution Spray Rate | 10 g/min | 10 g/min | 3 g/min |
| Atomization Air Pressure | 2 to 3 bar | 2.2 bar | 2.0 bar |
| Blowback Air Pressure | 0 bar | 0 bar | 0 bar |
| Fluidization Air Rate | 120 m$^3$/hr | 120 m$^3$/hr | 120 m$^3$/hr |

The coatings formed in the manner described above were dense. The sucrose/methocel precoat was 285 μm thick, the semipermeable cellulose acetate butyrate was 730 μm thick, and the pH coat was 460 μm thick.

EXAMPLE 3

FORMATION OF pH-TRIGGERED MEMBRANE TABLET COATINGS APPLIED BY DIP-COATING

A pH-triggered coating solution was made of 3.2 wt. % polymethyl methacrylate V920 (Rohm Haas), 12.8 wt. % Eudragit S-100 (Rohm Pharma), and 16 wt. % citric acid dissolved in acetone. The solution was stored in a sealed container at room temperature until used.

Pseudoephedrine tablets made by standard direct-compression techniques and consisting of 7 wt. % pseudoephedrine, 40 wt. % lactose, 40 wt. % Avicel pH101 (FMC Corp,), 5 wt. % AcDiSol (FMC Corp.), and 8 wt. % Remazol yellow (American Hoechst Corp.) (total weight of 350 mg) were dip-coated repeatedly by immersing them in the coating solution and withdrawing them slowly (about three seconds to completely withdraw a tablet). With each coating the tablets were allowed to air dry at room temperature. The tablets were dip-coated repeatedly starting with a coat of 15 wt. % Eudragit L (Rohm Pharma.) dissolved in ethanol. This Eudragit L coat was applied to the tablet to prevent the polyvinyl alcohol precoat solution from swelling the tablet core. After the Eudragit L coat, the tablet was ready for the precoat. The precoat consisted of two coats of 20 wt. % polyvinyl alcohol (Elvanol 51-05, DuPont Co., Wilmington, Del.) dissolved in deionized water then a single semipermeable coat of 15 wt. % cellulose acetate 398-10 (Eastman Chemical Products, Inc.) dissolved in acetone was applied. Another coat of polyvinyl alcohol was applied to prevent the pH-triggered coat solvent from redissolving the semipermeable coat. The final three coats were applied using the pH-triggered solution described above.

The coatings formed in the manner described above were dense. The polyvinyl alcohol precoat (120 μm thick) provided a smooth substrate for the next layer, which was the 75 μm cellulose acetate semipermeable layer. Another 75 μm coat of polyvinyl alcohol was applied to prevent the pH-triggered coating solvent from dissolving the semipermeable coat. This was necessary, since with the dip-coating method the previous coat is in contact with the solvent of the next coat for a significant amount of time. Finally, three coats of the pH-triggered membrane were applied with each of the three coats being approximately 130 μm thick.

EXAMPLE 4

FORMATION OF pH-TRIGGERED CAPSULE-SEAL

Capsules were made with a pH-triggered seal. A seal solution of 4.8 wt. % polymethyl methacrylate V920 (Rohm Haas), 19.0 wt. % Eudragit S-100 (Rohm Pharma.), and a trace of Bordeaux Red dye (Atlantic) dissolved in acetone was stored in a sealed container at room temperature until used. The trigger-pH is believed to range from 6.5 to 7.5 for the capsule seal material described in this example.

Capsules were formed by dip-coating aluminum mandrels with a polymer solution and then quenching the solution to precipitate the polymer. These capsules were made of ethylene vinyl alcohol copolymer (EVAL-F Co. of America) and consisted of a porous substrate with a thin, dense outer layer (i.e., asymmetric-type capsule walls). These capsules were semipermeable in that they were permeable to water and substantially impermeable to the excipients and drug in the capsule core. The EVAL-F capsules were made from a solution of 15 wt. % EVAL-F dissolved in a solution of 65 wt. % ethanol and 35 wt. % water. The mandrel was dipped into the coating solution and withdrawn slowly (about 7 seconds to completely withdraw the mandrel) then allowed to air dry for 7 seconds before being quenched in a 25° C. water bath for 30 minutes. The coating was then allowed to air dry for 2 hours before the outer, thin, dense EVAL-F coating was applied. The thin, dense EVAL-F coatings were made from a solution of 7.5 wt. % EVAL-F dissolved in a solution of 65 wt. % ethanol and 35 wt. % water, and maintained at 40° C. The coated mandrel was dipped into the coating solution, then air dried for at least 15 hours. The capsules were taken off the mandrels when dry and cut for length. A core consisting of 50 wt. % AcDiSol, 45 wt. % dextrose, and 5 wt. % dextran blue was loaded into the capsule body.

The capsules were sealed with the pH-triggered membrane solution described above. The capsules were sealed by rotating the capsules as a thin stream of sealing material was forced out of a syringe needle. The seal was applied completely around the joint and allowed to air dry at room temperature. Capsule seals formed by this process ranged in weight from 3 to 6 mg.

Example 4 demonstrates formation of a pH-triggered membrane seal on a semipermeable asymmetric capsule made by dip-coating. Capsule bodies were also made from cellulose acetate and polyurethane (formed by the same dip-coating process). The seal was also made using analogous procedures with 1:9, 1:5 and 1:4 ratios of PMMA V-920 and Eudragit S-100.

EXAMPLE 5

FORMATION OF pH-TRIGGERED MEMBRANE BEAD COATINGS APPLIED BY SPRAY COATING

A pH-triggered coating solution was made of 2.5 wt. % cellulose acetate 398-10 (Eastman Chemical Products, Inc.) and 2.5 wt. % cellulose acetate phthalate CD-910 (FMC Corp.) dissolved in acetone. The solution was stored in a sealed container at room temperature until used. The trigger-pH is believed to range from 5.5 to 7.5 for the coating described in this example.

Pseudoephedrine beads were made by coating a drug slurry onto 16-20 mesh Nu-Pareils (Ingredient Technology Corporation) using the STREA-1 spray coater (Aeromatic). The drug slurry consisted of 1.4 wt. % pseudoephedrine, 2.05 wt. % sucrose, 2.05 wt. % Methocel E6 Premium (Dow Chemical Co.), 4.0 wt. % Avicel pH101 (FMC Corp.) and 0.5 wt. % AcDiSol (FMC Corp.) dissolved and suspended in deionized water. The drug-slurry coated beads were then spray coated using the STREA-1 with a solution of 5 wt. % cellulose acetate 398-3 (Eastman Chemical Products, Inc.) dissolved in acetone (forming a semipermeable coating). Finally, the beads were spray coated using the STREA-1 with the pH-triggered coating solution described above. The pH-triggered coated bead contained 1.8 wt. % pseudoephedrine with 12.5 wt. % semipermeable coating and 38.8 wt. % pH-triggered coating.

Equipment: STREA-1 with plexiglass bowl for precoat, and stainless steel wurster bowl (without pipe support) for semipermeable and pH-triggered coats, 1 mm nozzle, peristaltic pump, balance, and 90 psi house air supply.

| Spray Conditions: | Precoat | Semipermeable | pH-triggered |
|---|---|---|---|
| Sample Size | 200.07 g | 266.10 g | 115.07 g |
| Heater Setting | 92° C. | 54° C. | 55° C. |
| Feed-Solution Spray Rate | 13.5 g/min | 10 g/min | 11 g/min |
| Atomization Air Pressure | 2.0 bar | 2.2 bar | 2.2 bar |
| Blowback Air Pressure | 0 bar | 0 bar | 0 bar |
| Fluidation Air Rate | 140 m³/hr | 140 m³/hr | 140 m³/hr |

The coatings formed in the manner described above were dense. The drug layer was approximately 100 μm thick, the semipermeable coat was 60 μm thick, and the pH-triggered coat was about 125 μm thick.

EXAMPLE 6

FORMATION OF pH-TRIGGERED MEMBRANE FLAT SHEETS pH-triggered polymer solutions were prepared by mixing pH-sensitive polymers with nondissolving materials. The pH-sensitive polymer tested was Eudragit S-100 (Rohm Pharma.). The nondissolving polymers tested were Eudragit RL (Rohm Pharma) and polymethyl methacrylate PMMA V920 (Rohm Haas). Films were made of these materials by dissolving them in acetone, casting the solution on a glass plate, and then allowing the acetone to evaporate. The trigger-pH is believed to range from 4.5 to 7 for all of the films described in this example.

Polymer films (~50 μm thick) were cut into 1- to 2-cm-wide strips and were suspended vertically in buffer solution with a weight attached, such that 10 psi of tensile stress was applied. The buffer was unstirred to minimize additional stress on the films. The time required to break the films (break time) was determined by visual observation. These films, elongated and broke in intestinal buffer, rather than dissolving as would conventional enteric coating films. The stability of the polymer films was tested by exposing the films to gastric buffer (pH 1.5) containing sodium chloride, hydrochloric acid, and sodium hydroxide with an osmotic pressure of 7 atms. for 20 hours. None of the films broke during the stability test. The films were then tested in intestinal buffer (pH 7.5) containing potassium phosphate, monobasic, and sodium hydroxide with an osmotic pressure of 7 atm. and the break times recorded.

These flat sheets were made as a screening test to determine how polymers or polymer blends function as degradable seals (for capsule) when exposed to changes in pH.

Several pH-triggered polymer films were prepared from solutions made by varying the amounts of pH-sensitive polymers mixed with nondissolving polymers. Films were made of pH-sensitive polymers, including cellulose acetate phthalate (CAP), cellulose acetate trimellitate (CAT), and Eudgragit S-100. Films were also made that consisted of the following polymer blends: 1) CAP and cellulose acetate (CA 398-10) blends with ratios of 60/40, 80/20, 85/15, and 90/10; 2) CAT and CA 398-10 blends with ratios of 80/20, 85/15, 90/10, and 95/5; 3) Eudragit S-100 and CA 398-10 blends with ratios of 70/30, 80/20, and 90/10; 4) Eudragit S-100 and Eudragit RL blends with ratios of 80/20 and 90/10; 5) Eudragit S-100 and Eudragit RS blends with ratios of 70/30, 80/20, and 90/10; and 6) Eudragit S-100 and PMMA V920 blends with ratios of 50/50, 70/30, 80/20, and 90/10.

Figure 3:
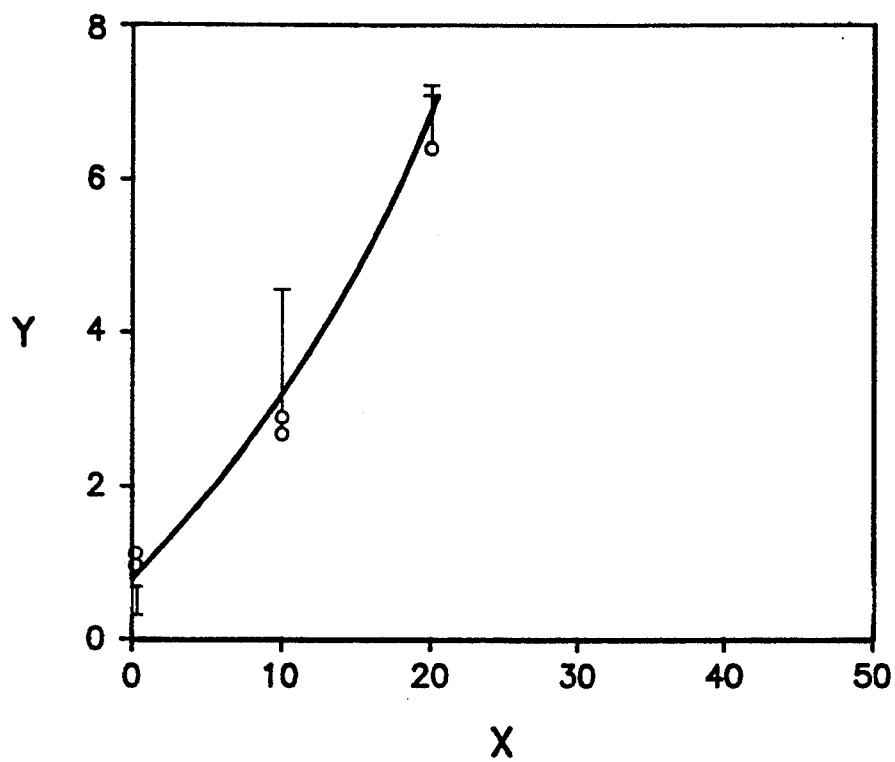
FIG. 3 is a graph of break times and ranges for blended Eudragit RL/Eudragit S-100 films immersed in intestinal buffer.
Figure 4:
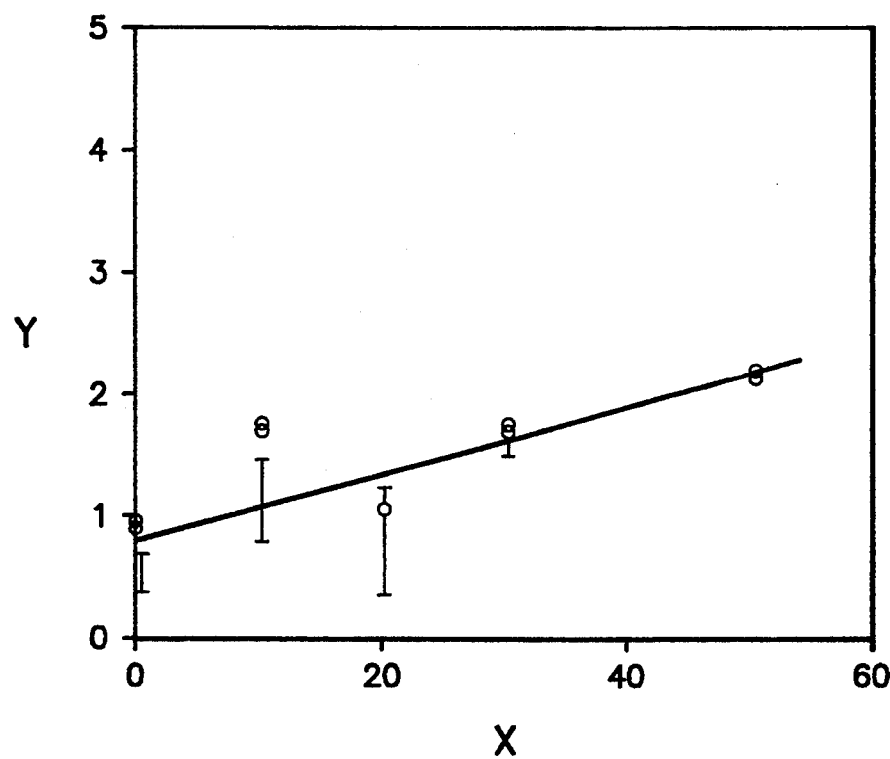
FIG. 4 is a graph of break times and ranges for blended PMMA/Eudragit S-100 films immersed in intestinal buffer.

These films were tested in gastric buffer to determine break times. Results from these tests showed that the break times increase as the content of nondissolving polymer increases. The break times are shown in FIGS. 3 and 4 in which break time in hours (Y) is graphed against Eudragit RL wt. %, in Eudragit RL and Eudragit S-100 polymer blends, and PMMA V920 wt. %, in PMMA V920 and Eudragit S-100 polymer blends (X), respectively. Similar results were observed for the other polymer blends. As the CA 398-10 content increased from 10 wt. % to 40 wt. % the break times went from less than one hour to greater than 21 hours. Likewise CA 398-10/CAT films containing 20 wt. % CA 398-10 exhibited break times of greater than 3 hours. Films consisting of CA 398-10 and Eudragit S-100 were very brittle and at high CA 398-10 content were incompatible. The break times from these films were unusual in that there was a local maximum (for films containing 0 wt. % to 30 wt. % CA 398-10) break time of two hours with films containing 10 wt. % CA 398-10. The break times for the films consisting of Eudragit RS and Eudragit S-100 were similar to the break times shown in FIG. 3 for Eudragit RL/Eudragit S-100 films.

Results from these tests with polymer films indicate that the break time and corresponding delivery site can be controlled by the ratio of pH-sensitive polymer to nondissolving polymer.

EXAMPLE 7

Figure 5:
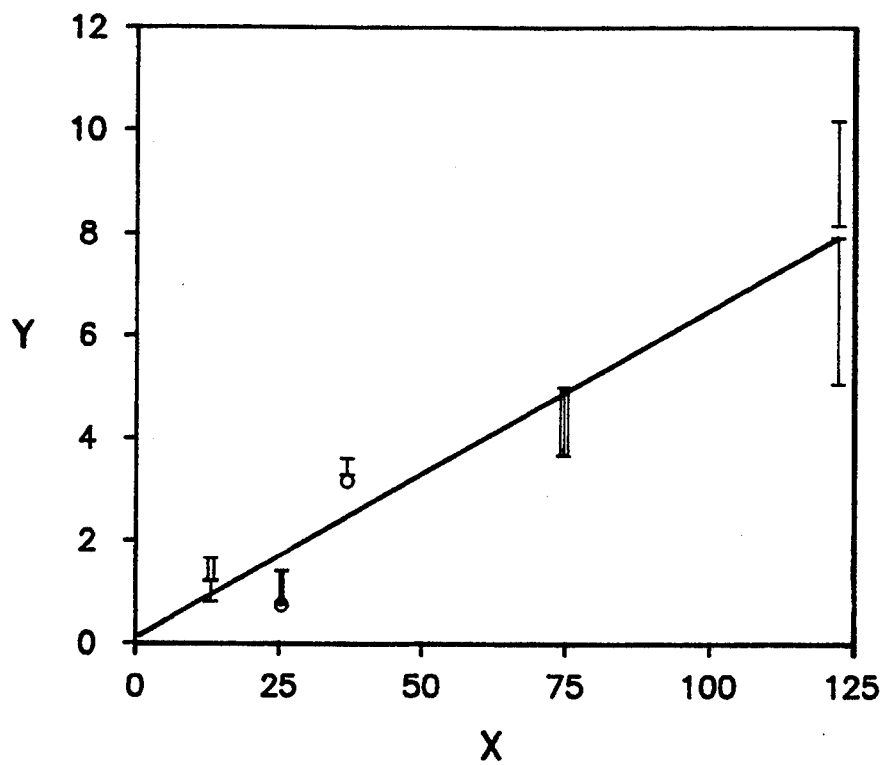
FIG. 5 is a graph of break times and ranges for films consisting of 20% PMMA and 80% Eudragit S-100 immersed in intestinal buffer.

BREAK TIME CAN BE CONTROLLED BY THICKNESS OF pH-TRIGGERED MEMBRANE pH-Triggered polymer films were made using 80 wt. % Eudragit S-100 (Rohm Pharma.) and 20 wt. % polymethyl methacrylate PMMA V-920 (Rohm Haas). The trigger-pH is believed to range from 6.5 to 7.5 for the films described in this example. The pH-triggered polymer films were made at various thicknesses by the process described in Example 6. The break times and corresponding film thicknesses are shown in FIG. 5 in which break time (hours) Y is plotted against film thickness ($\mu$m) X. The burst time and corresponding intestinal delivery site can be controlled by the thickness of the pH-triggered coat. As shown in this Example, burst time of the films are proportional to thickness.

EXAMPLE 8

RELEASE OF PSEUDOEpHEDRINE FROM pH-TRIGGERED MEMBRANE COATED TABLETS

Pseudoephedrine tablets made by standard direct-compression techniques had a total weight of 350 mg and consisted of 14 wt. % pseudoephedrine, 41 wt. % lactose, 40 wt. % Avicel pH101 (FMC Corp.) and 5 wt. % AcDiSol (FMC Corp.). These tablets were coated with a semipermeable coating consisting of CA 398-3 as described in Example 1. These tablets were then coated with a pH-triggered membrane coating analogously to the coating described in Example 1.

Figure 6:
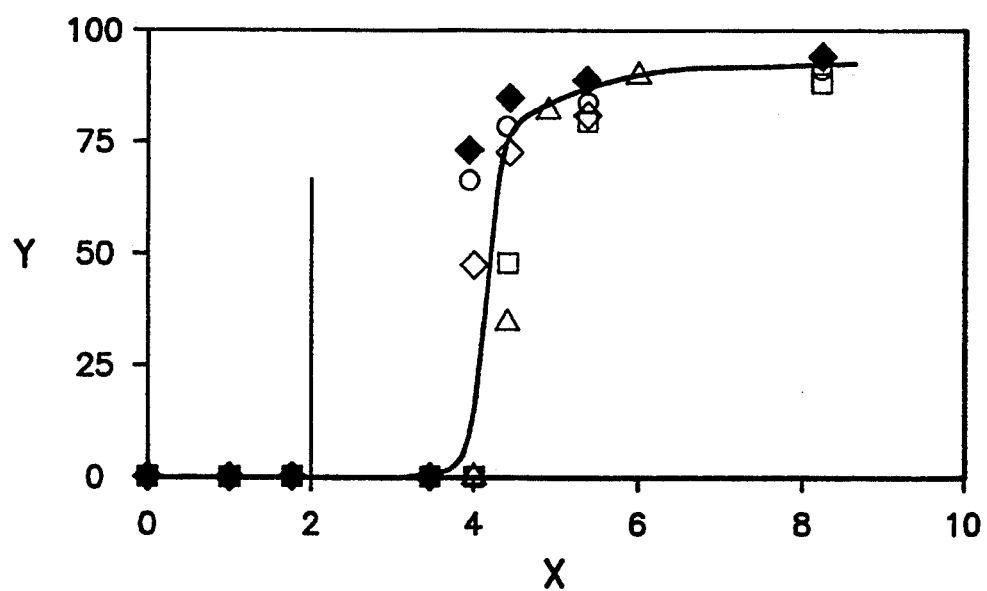
FIG. 6 is a release-rate graph showing burst of pseudoephedrine from tablets coated with 30/70 CNCAP and tested in pH 1.2 gastric buffer then transferred to intestinal buffer.
Figure 6:
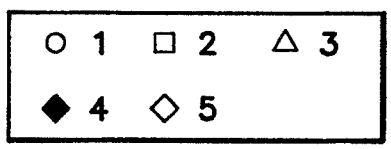
Figure 7:
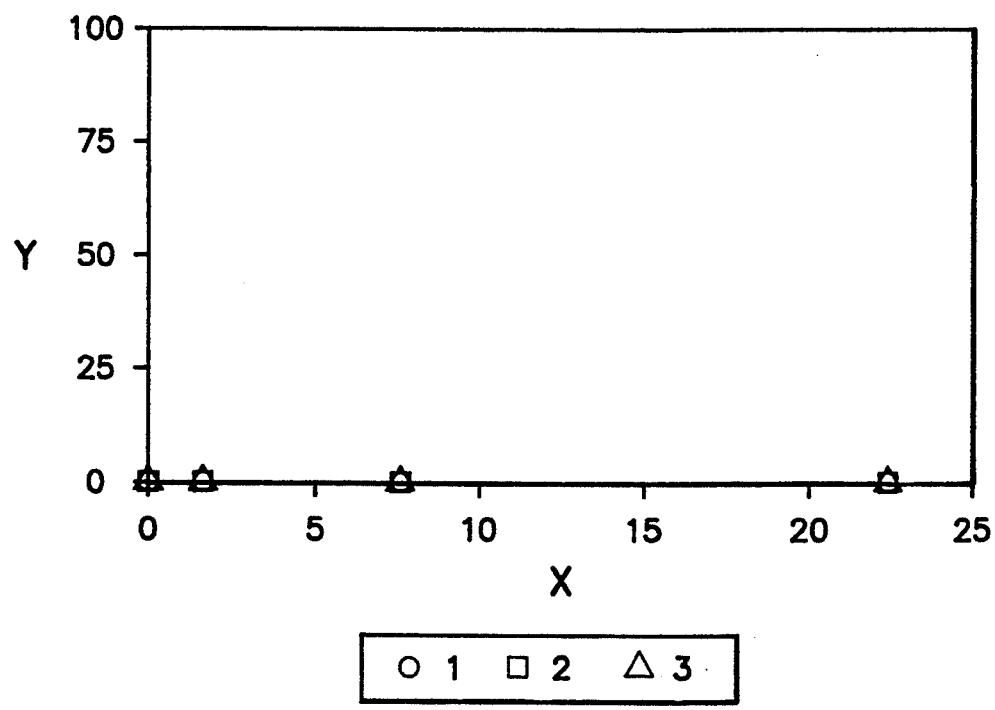
FIG. 7 is a release-rate graph for tablets coated with 30/70 CA/CAP tested as controls in pH 1.2 gastric buffer.

Release-rate tests were conducted in gastric and intestinal buffers at 37° C. with continuous stirring at 150 rpm. The gastric-and intestinal-buffer solutions are described in Example 6. Pseudoephedrine solubility was greater than 500 mg/ml in both the gastric and intestinal buffers. The tablets were placed in 350 ml gastric buffer for two hours and then transferred to 400 ml intestinal buffer. The tablets burst approximately 2 hours after being transferred to intestinal buffer, releasing virtually all the pseudoephedrine contained in the tablets. Similar tablets remained in 350 ml gastric buffer throughout the test to serve as controls. These tablets did not release any pseudoephedrine for at least 23 hours. FIG. 6 graphs % of total Pseudoephedrine released (Y) against time in hours (X) for the five repetitions denoted by the five symbols. FIG. 7 graphs % of total pseudoephedrine released (Y) against time in hours (X) for three gastric controls repetitions.

Example 8 demonstrates triggered release from tablets coated with the pH-triggered membrane coating. With these coatings, drugs can be delivered to specific intestinal sites.

EXAMPLE 9

RELEASE OF PSEUDOEpHEDRINE FROM CAPSULES WITH A pH-TRIGGERED MEMBRANE SEAL

Capsule bodies and seal solutions were made as described in Example 4. The capsules were loaded with 75/25 AcDiSol (FMC Corp.)/dextrose filler and a 50/50 cocoa butter/pseudoephedrine mixture formed into a plug and coated with cellulose acetate trimellitate (Eastman Chemical Products, Inc.) and Eudragit S-100 (Rohm Pharma.).

Figure 8:
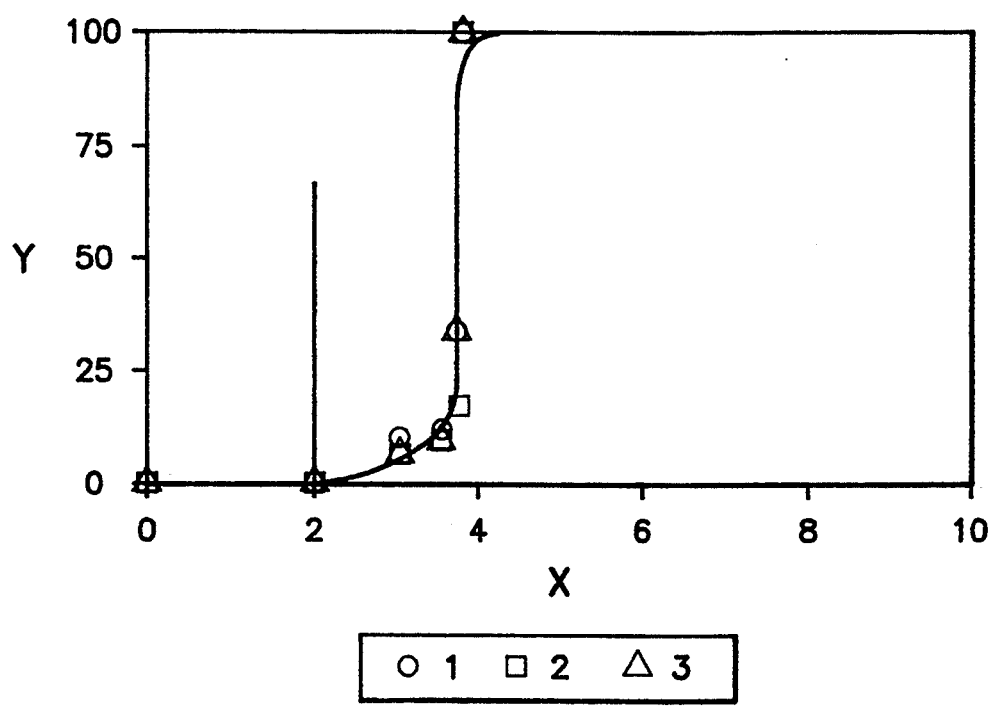
FIG. 8 is a release-rate graph showing burst of pseudoephedrine from capsule with 20/80 PMMNEudragit S-100 pH-triggered membrane seal tested in pH 1.2 gastric buffer then transferred to intestinal buffer.
Figure 9:
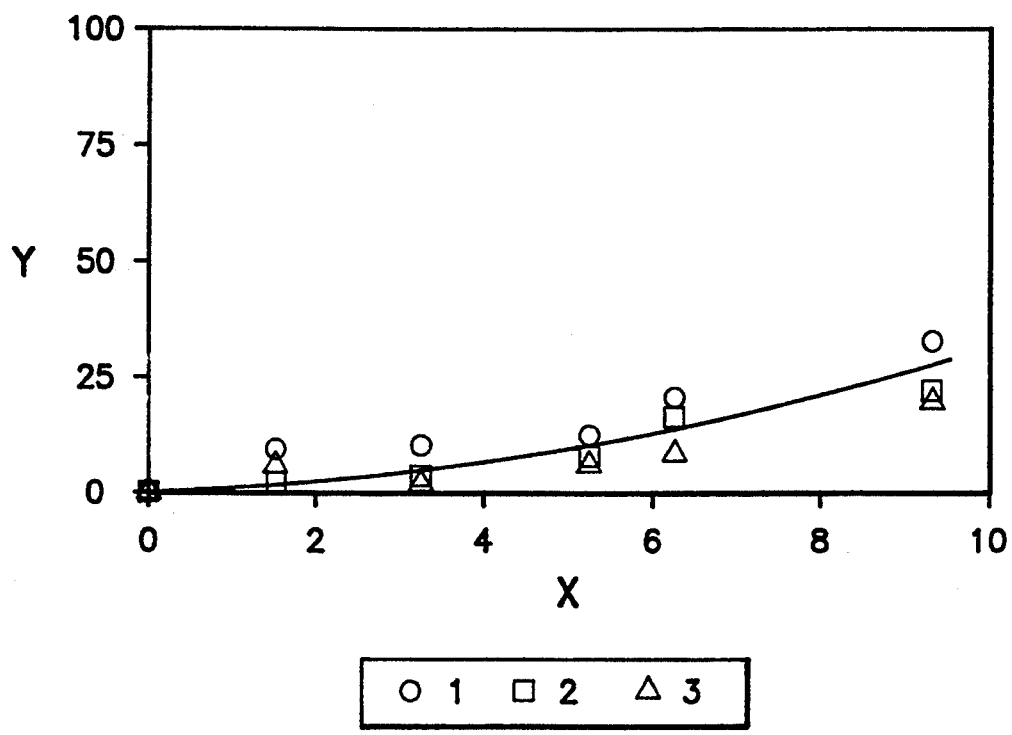
FIG. 9 is a release-rate graph showing very little pseudoephedrine released from capsules with a 20/80 PMMNEudragit S-100 pH-triggered membrane seal tested in pH 1.2 gastric buffer.

Release-rate tests were conducted in gastric and intestinal buffers at 37° C. with continuous stirring. The gastric- and intestinal-buffer solutions are described in Example 6. Pseudoephedrine solubility is greater than 500 mg/ml in both gastric and intestinal buffers. The capsules were placed in 100 ml intestinal buffer. The capsules burst approximately 2 hours after being transferred to intestinal buffer, releasing virtually all the pseudoephedrine contained in the capsules. Similar capsules remained in 100 ml gastric buffer throughout the test to serve as controls. These capsules did not begin to release any pseudoephedrine until after they had been in the gastric buffer for 5 hours. FIG. 8 graphs % of total pseudoephedrine released (Y) against time in hours (X) for the three repetitions denoted by the three symbols. FIG. 9 graphs % of total pseudoephedrine released (Y) against time in hours (X) for three gastric control repetitions.

Example 9 demonstrates triggered release from capsules with pH-triggered membrane seals. With these coatings, drugs can be delivered to specific intestinal sites.

EXAMPLE 10

RELEASE OF PSEUDOEpHEDRINE FROM pH-TRIGGERED MEMBRANE COATED BEADS

Pseudoephedrine beads were made by spray coating a drug slurry onto 16-20 mesh Nu-Pareils (Ingredient Technology Corporation) as described in Example 5. These beads were coated with a pH-triggered membrane coating using an analogous process to the one described in Example 5. The pH-triggered coated beads had a pseudoephedrine loading of 18.5 mg/g beads with 12.5 wt. % semipermeable coating consisting of CA398-3 and 39 wt. % pH-triggered coating consisting of CAP and CA 398-10 in a 1:1 ratio.

Figure 10:
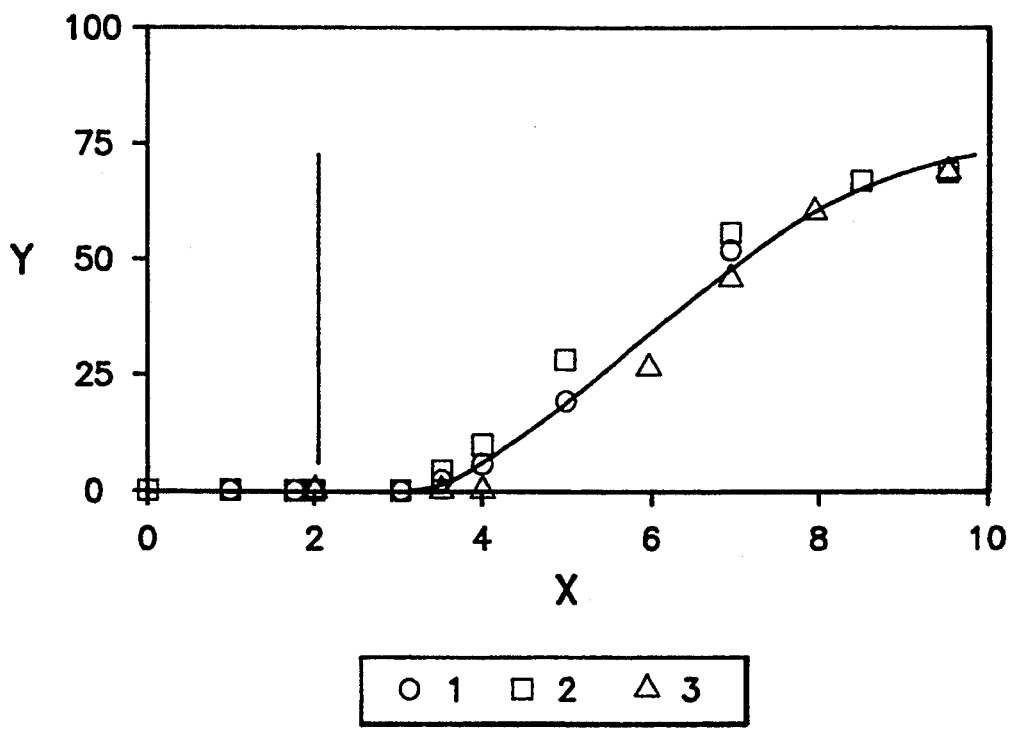
FIG. 10 is a release-rate graph showing delivery of pseudoephedrine with 50/50 CNCAP pH-triggered membrane coating tested in pH 1.2 gastric buffer then transferred to intestinal buffer.

Release-rate tests were conducted in gastric and intestinal buffers at 37° C. with continuous stirring. The gastric and intestinal buffer solutions are described in Example 6. Pseudoephedrine solubility is greater than 500 mg/ml in both gastric and intestinal buffers. The beads burst approximately 1.5 to 2 hours after being transferred to intestinal buffer. FIG. 10 graphs % of total pseudoephedrine released (Y) against time in hours (X) for the three repetitions denoted by the three symbols.

Example 10 demonstrates triggered release from beads with pH-triggered membrane seals. With these coatings, drugs can be delivered to specific intestinal sites.

EXAMPLE 11

TABLET BURST TIME CAN BE CONTROLLED BY THICKNESS OF pH-TRIGGERED MEMBRANE COATING pH-Triggered coating solutions made of 50/50 cellulose acetate 398-10 (Eastman Chemical Products, Inc.)/cellulose acetate phthalate CD-910 (FMC Corp.) dissolved in acetone were stored in a sealed container at room temperature until used. The trigger-pH is believed to range from 5.5 to 7.5 for the coating described in this example.

Pseudoephedrine tablets made by standard direct-compression techniques had a total weight of 350 mg and consisted of 14 wt. % pseudoephedrine, 40 wt. % lactose, 40 wt. % Avicel pH101 (FMC Corp.), 5 wt. % AcDiSol (FMC Corp.), and 1 wt. % acid black. These tablets were coated with a 9 mg/tablet semipermeable coat consisting of CA 398-3 as described in Example 1. The pH-triggered coating solution described above was applied at various thicknesses of 70 $\mu$m, 125 $\mu$m, and 170 $\mu$m, as determined by scanning electron microscope (SEM) observation. Another set of pseudoephedrine tablets made the same way, but consisting of 14 wt. % pseudoephedrine, 41 wt. % lactose, 40 wt. % Avicel pH101 (FMC Corp.), and 5 wt. % AcDiSol (FMC Corp.) were coated with a 4 mg/tablet semipermeable coat. These tablets were coated using the pH-triggered coating solution described above to get a coating thickness of about 35 $\mu$m.

Figure 11:
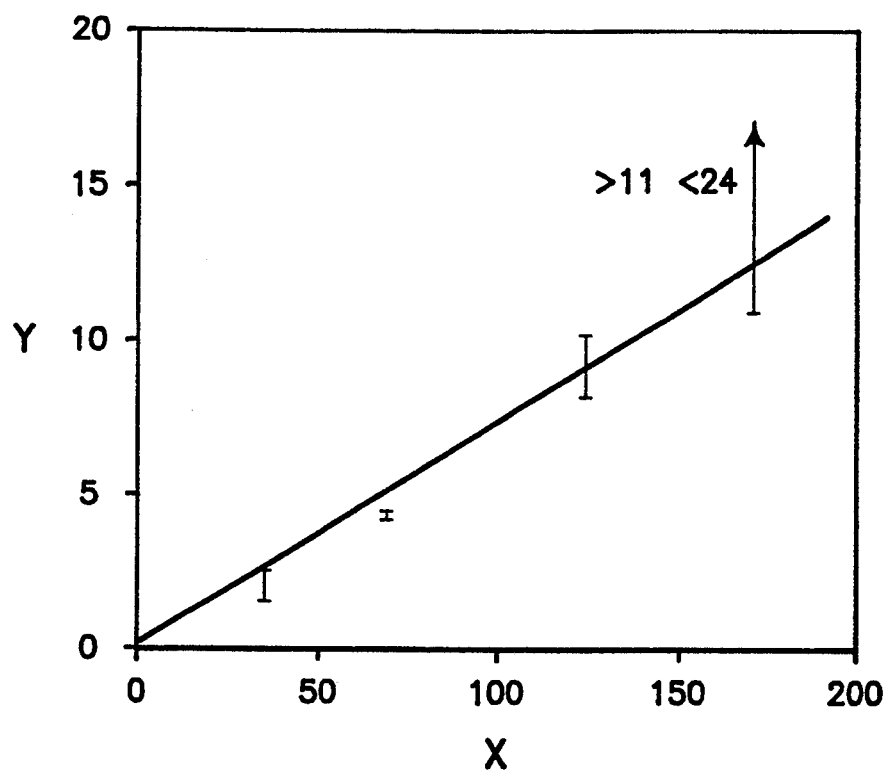
FIG. 11 is a graph of burst times vs. coating thickness for 50/50 CA/CAP pH-triggered membrane coated tablets tested in pH 1.2 gastric buffer then transferred to intestinal buffer.

Burst times were determined from these tablets by running release-rate tests in gastric and intestinal buffers as described in Example 8. The burst times for tablets with pH-triggered membrane coatings of various thicknesses are shown in FIG. 11. The last data point had a burst time of between 11 and 24 hours. Burst times increased as the thickness of the coatings increased. In FIG. 11, burst time in hours (Y) is graphed against coating thickness in $\mu$m (X).

Example 11 demonstrates that the burst time and corresponding intestinal delivery site can be controlled by the thickness of the pH-triggered coat.

EXAMPLE 12

TABLET BURST TIME CAN BE CONTROLLED BY THE RATIO OF pH-SENSITIVE POLYMER TO NONDISSOLVING MATERIAL IN THE pH-TRIGGERED MEMBRANE COATING pH-Triggered coating solutions made of cellulose acetate 398-10 (Eastman Chemical Products, Inc.) and cellulose acetate phthalate CD-910 (FMC Corp.) dissolved in acetone were stored in a sealed container at room temperature until used. The trigger-pH is believed to range from 5.5 to 7.5 for the coating described in this example.

Pseudoephedrine tablets made by standard direct-compression techniques as described in Example 11 and coated with a CA 398-3 semipermeable coating were coated with pH-triggered coating solutions of cellulose acetate 398-10 (Eastman Chemical Products, Inc.) and cellulose acetate phthalate CD-910 (FMC Corp.) dissolved in acetone where the ratio of pH-sensitive polymer to nondissolving material varied. The tablets were coated with the pH-triggered coating solutions as described in Example 1.

Figure 12:
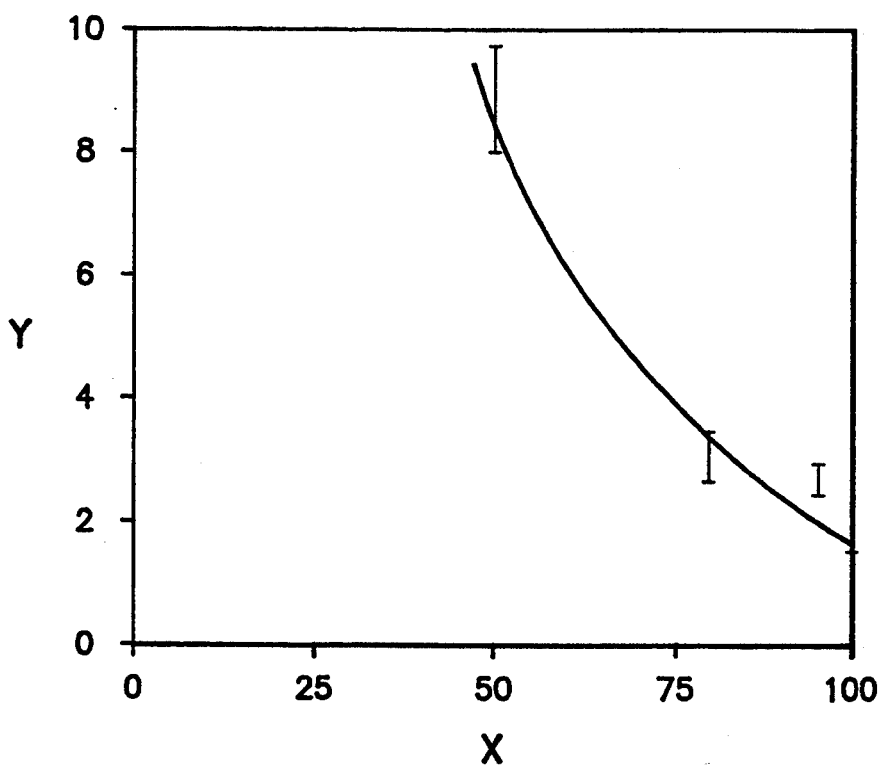
FIG. 12 is a graph of burst times for tablets in intestinal buffer with coatings made using different ratios of CA to CAP.

Burst times were determined from these tablets by running release-rate tests in gastric and intestinal buffers as described in Example 8. The burst times for tablets with varying ratios of pH-sensitive polymer is shown in FIG. 12. Burst times decrease as the content of pH-sensitive material in the coating increases. In FIG. 12, burst time in hours (Y) is graphed against % cellulose acetate phthalate content (X).

Example 12 demonstrates that the burst time and corresponding intestinal delivery site can be controlled by the ratio of pH-sensitive polymer to nondissolving material in the pH-triggered coat.

EXAMPLE 13

CAPSULE BURST TIME CAN BE CONTROLLED BY THE RATIO OF pH-SENSITIVE POLYMER TO NONDISSOLVING MATERIAL IN THE pH-TRIGGERED MEMBRANE SEAL

Capsules were made with pH-triggered membrane seals as described in Example 4. Seal solutions were made where the ratio of pH-sensitive polymer (Eudragit S-100, Rohm Pharma.) to nondissolving material (polymethyl methacrylate, PMMA V-920, Rohm Haas) was varied.

Figure 13:
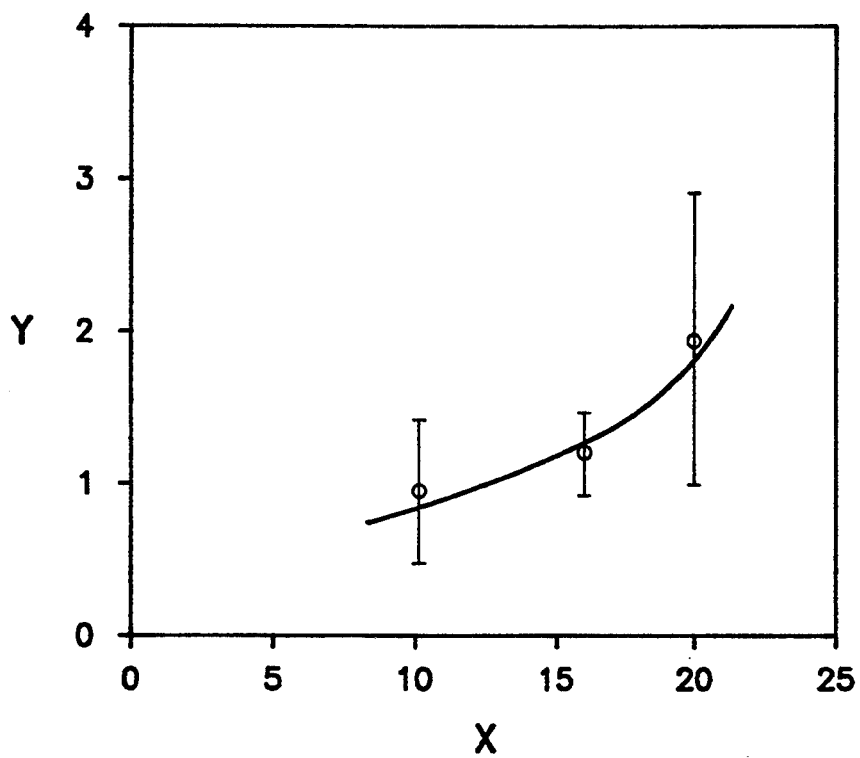
FIG. 13 is a graph of burst times for capsules in intestinal buffer with seals made using different concentrations of PMMA and Eudragit S-100.

Release-rate tests were conducted as described in Example 9 to determine the capsule burst times. The burst times for the pH-triggered membrane sealed capsules with varying ratios of pH-sensitive polymer are shown in FIG. 13. FIG. 13 graphs burst time in intestinal buffer in hours (Y) against weight % of PMMA V920 in capsule seals (X).

Example 13 demonstrates that the burst time and corresponding intestinal delivery site can be controlled by the ratio of pH-sensitive polymer to nondissolving material in the pH-triggered capsule seal.

EXAMPLE 14

TABLET BURST TIME CAN BE CONTROLLED BY BOTH THE COATING THICKNESS AND THE RATIO OF pH-SENSITIVE POLYMER TO NONDISSOLVING MATERIAL IN THE pH-TRIGGERED MEMBRANE COATING pH-Triggered coating solutions made of cellulose acetate 398-10 (Eastman Chemical Products, Inc.) and cellulose acetate phthalate CD-910 (FMC Corp.) dissolved in acetone were stored in a sealed container at room temperature until used.

Pseudoephedrine tablets made by standard direct-compression techniques and coated with a CA 398-3 semipermeable coating as described in Example 11 were coated with pH-triggered coating solutions of cellulose acetate 398-10 (Eastman Chemical Products, Inc.) and cellulose acetate phthalate CD-910 (FMC Corp.) dissolved in acetone where both the coating thickness and the ratio of pH-sensitive polymer to nondissolving material was varied. The tablets were coated with the pH-triggered coating solutions as described in Example 1.

Figure 14:
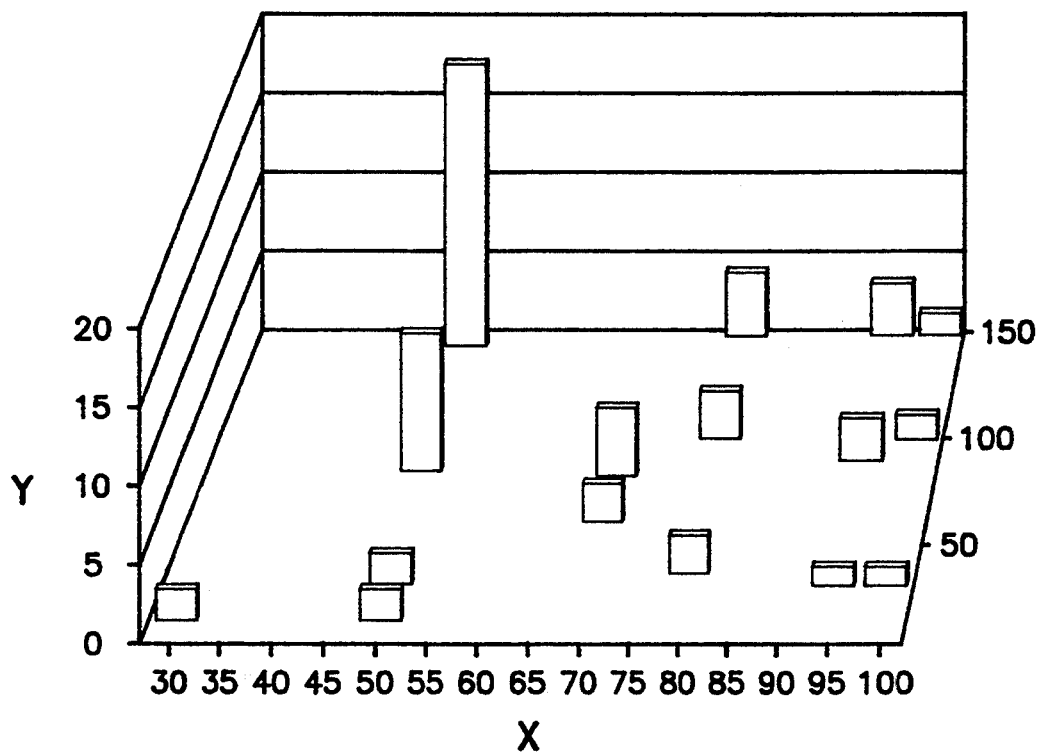
FIG. 14 is a graph of burst times for tablets in intestinal buffer with coatings of various thicknesses and CAP content.

Burst times were determined from these tablets by running release rate tests into gastric and intestinal buffers as described in Example 8. The burst times for tablets with varying thickness and ratio of pH-sensitive polymer is shown in FIG. 14. FIG. 14 graphs burst time in hours (Y) vs. weight % cellulose acetate phthalate (X) vs. coating thickness in $\mu$m (Z).

Example 14 demonstrates that the burst time and corresponding intestine site of delivery can be controlled by both the coating thickness and the ratio of sensitive polymer to nondissolving material in the pH-triggered coat.

EXAMPLE 15

TABLET BURST TIME AFTER TRANSFER INTO INTESTINAL BUFFER IS INDEPENDENT OF TIME SPENT IN GASTRIC BUFFER

Pseudoephedrine tablets made by standard direct-compression techniques and coated with a CA 398-3 semipermeable coating as described in Example 11 were coated with pH-triggered coating solutions of 30 wt. % cellulose acetate 398-10 (Eastman Chemical Products, Inc.) and 70 wt. % cellulose acetate phthalate CD-910 (FMC Corp.) dissolved in acetone. The trigger-pH is believed to range from 5.5 to 7.5 for the coating described in this example. The tablets were coated with the pH-triggered coating solutions as described in Example 1.

Figure 15:
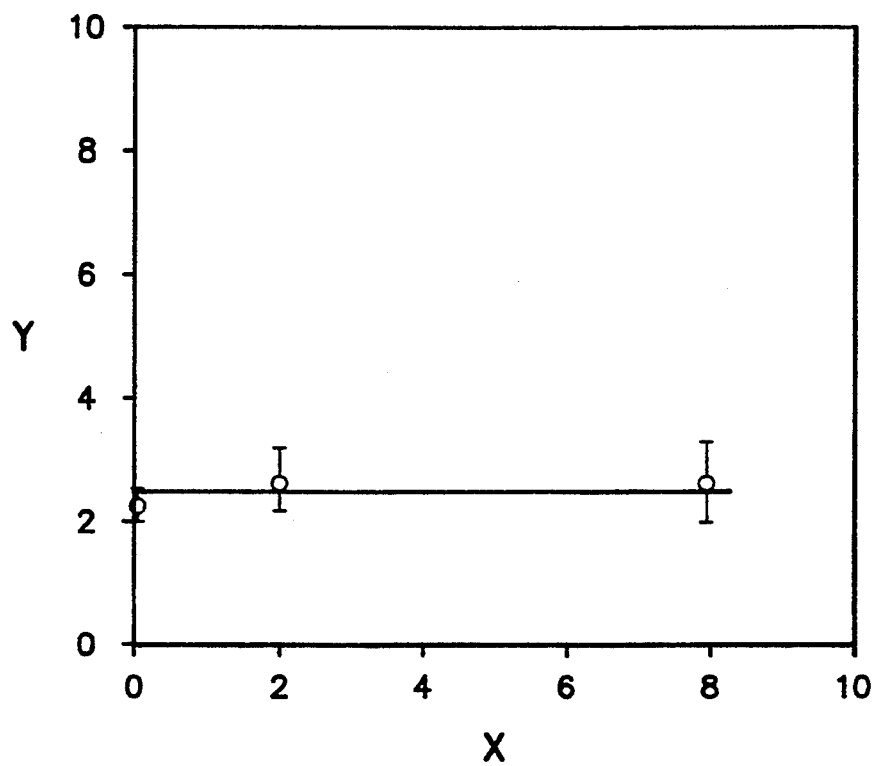
FIG. 15 is a graph of burst times for tablets coated with 30/70 CA/CAP vs. time in pH 1.2 gastric buffer prior to transfer to intestinal buffer.

Burst times were determined from these tablets by running release-rate tests in gastric and intestinal buffers as described in Example 7, except that the amount of time the tablets remained in gastric buffer was varied from 0 hours to 8 hours and then the tablets were transferred to intestinal buffer. The burst times for tablets with different gastric buffer exposure durations are shown in FIG. 15. FIG. 15 graphs burst time in intestinal buffer in hours (Y) against time in gastric buffer in hours (X).

Example 15 demonstrates that the burst time and corresponding intestinal delivery site is independent of the length of time the tablet remains in the stomach.

EXAMPLE 16

BEAD BURST TIME AFTER TRANSFER INTO INTESTINAL BUFFER IS INDEPENDENT OF TIME SPENT IN GASTRIC BUFFER

Pseudoephedrine beads were made by spray coating a drug slurry onto 16–20 mesh Nu-Pareils (Ingredient Technology Corporation) as described in Example 5. The pH-triggered coated beads had a pseudoephedrine loading of 18.5 mg/g beads with 12.5 wt. % semipermeable coating consisting of CA 398-3 and 39 wt. % pH-triggered coating consisting of a 50/50 blend of CAP and CA 398-10. The trigger-pH is believed to range from 5.5 to 7.5 for the coating described in this example.

Figure 16:
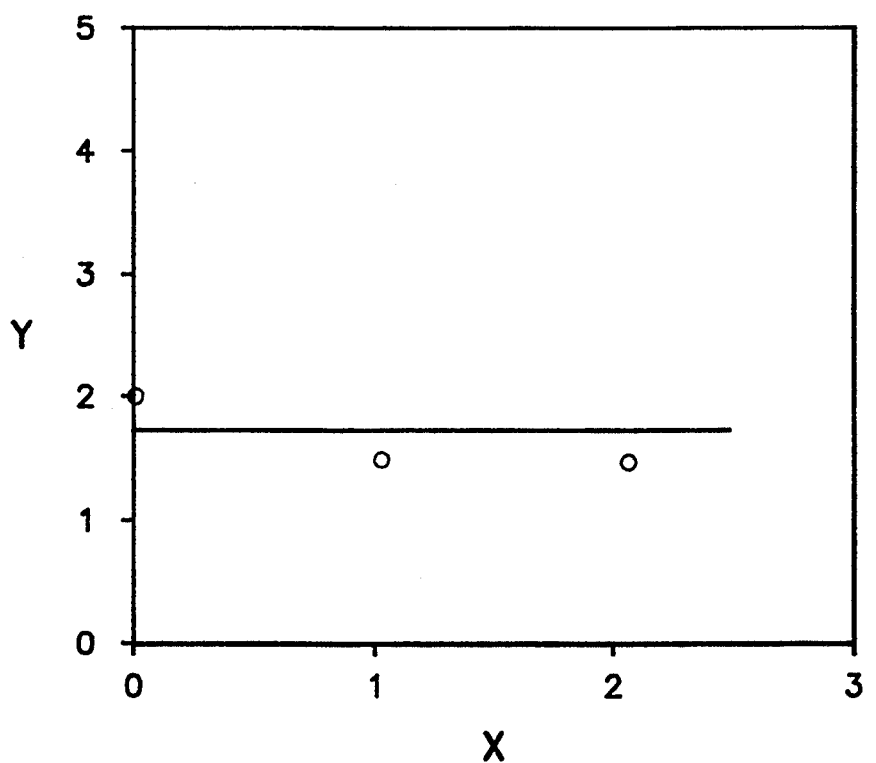
FIG. 16 is a graph of burst times for beads vs. time in pH 1.2 gastric buffer prior to transfer to intestinal buffer.

Burst times were determined from these beads by running release-rate tests into gastric and intestinal buffers as described in Example 15. The burst times for beads in intestinal buffer with different gastric buffer exposure durations are shown in FIG. 16. FIG. 16 graphs burst time in hours (Y) vs. time in gastric buffer in hours (X). Example 16 demonstrates that the burst time and corresponding intestinal delivery site is independent of the length of time the tablet remains in the stomach.

EXAMPLE 17

CAPSULE BURST TIME AFTER TRANSFER INTO INTESTINAL BUFFER IS INDEPENDENT OF TIME SPENT IN GASTRIC BUFFER

Figure 17:
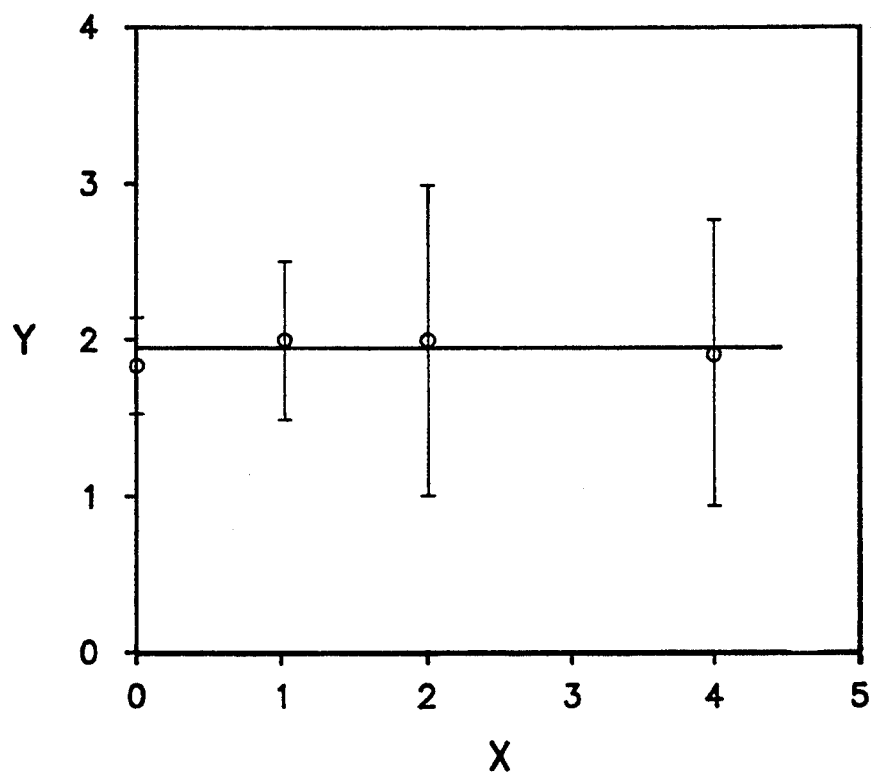
FIG. 17 is a graph of burst times for capsules in intestinal buffer after various times in pH 1.2 gastric buffer.

Capsules were made with pH-triggered membrane seals consisting of a 20/80 blend of PMMA V920 and Eudragit S-100 as described in Example 4. The capsule bodies were made of EVAL-F as described in Example 4. Burst times were determined from these capsules by running release-rate tests in gastric and intestinal buffers as described in Example 15, except that the amount of time the capsules remained in gastric buffer was varied from 0 hours to 4 hours. The burst times for capsules with different gastric-buffer exposure durations are shown in FIG. 17. FIG. 17 graphs burst time in intestinal buffer in hours (Y) against time in gastric buffer in hours (X).

Example 17 demonstrates that the burst time and corresponding intestinal delivery site is independent of the length of time the capsules remains in the stomach.

EXAMPLE 18

TABLET BURST TIME IN INTESTINAL BUFFER IS INDEPENDENT OF THE pH OF THE GASTRIC BUFFER

Pseudoephedrine tablets made by standard direct-compression techniques and coated with a CA 398-3 semipermeable coating (described in Example 11) were coated with pH-triggered coating solutions of 30 wt. % cellulose acetate 398-10 (Eastman Chemical Products, Inc.) and 70 wt. % cellulose acetate phthalate CD-910 (FMC Corp.) dissolved in acetone as described in Example 1.

Burst times were determined from these tablets by running release-rate tests in gastric and intestinal buffers as described in Example 8. Burst times were also determined for release rates with the gastric buffer pH up to 6. In both cases the burst times were around 2 hours. The burst times for tablets are independent of the pH of gastric buffer solutions.

Example 18 demonstrates that the burst time and corresponding intestinal delivery site is independent of the acidity of the stomach. This demonstrates that the trigger-pH for the coating described in this example is greater than 6 and less than 7.5.

EXAMPLE 19

BEAD BURST TIME IN INTESTINAL BUFFER IS INDEPENDENT OF THE pH OF THE GASTRIC BUFFER

Pseudoephedrine beads were made and coated with the same semipermeable pH-triggered membrane coatings as described in Example 5. Burst times were determined from these beads by running release-rate tests in gastric and intestinal buffers and described in Example 15. Burst times were also determined for beads placed in gastric buffer at a pH of 5.5 and then into intestinal buffer, in both cases the burst times in intestinal buffer were between 1-½ hours and 2 hours. The burst times for beads are independent of the gastric-buffer acidity.

Example 19 demonstrates that the burst time and corresponding intestinal delivery site is independent of the acidity of the stomach. This demonstrates that the trigger-pH for the coating described in this example is greater than 5.5 and less than 7.5.

EXAMPLE 20

DEMONSTRATION THAT THE SEMIPERMEABLE COAT IS NECESSARY TO PREVENT THE DRUG FROM LEAKING PREMATURELY

Tablets containing 14 wt. % pseudoephedrine, 41 wt % lactose, 40 wt. % Avicel pH101 (FMC Corp.) and 5 wt. % AcDiSol (FMC Corp.) (total weight of 350 mg) were coated with the sucrose/Methocel E6 precoat and then the cellulose acetate 398-3 semipermeable coat as described in Example 1.

Figure 18:
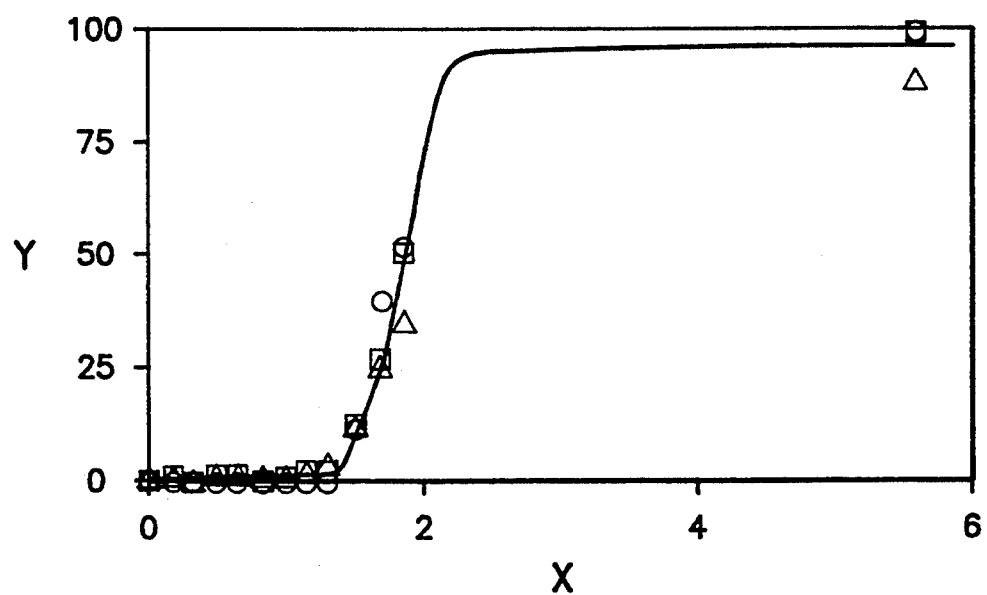
FIG. 18 is a release rate graph showing no pseudoephedrine released from tablets coated with a CA semipermeable coating prior to bursting at about 1.5 hour.

The semipermeable coat is necessary to prevent the drug from leaking prematurely. Drug leakage prior to release is a common problem with conventional enteric coatings. The semipermeable coat allows water to permeate into the tablet, but at the same time will contain the excipients and drug within the tablet core. The drug release rate profile was determined from these semipermeable coated tablets in intestinal buffer at 37° C. The intestinal buffer contained potassium phosphate, monobasic, and sodium hydroxide, and had a pH of 7.5 and an osmotic pressure of 7 atm. None of the drug was released prior to the semipermeable coating splitting open at about 1-½ hours (FIG. 18). FIG. 18 graphs % of total drug released (Y) vs. time in hours (X) for three tablets denoted by the three different symbols. Example 20 demonstrates that the semipermeable coat facilitates the prevention of premature drug leakage.

EXAMPLE 21

TABLET BURST TIME IS DETERMINED BY A CHANGE IN COATING PERMEABILITY AND STRENGTH TRIGGERED BY A CHANGE IN pH

Pseudoephedrine tablets made by standard direct-compression techniques and coated with a CA 398-3 semipermeable coating were coated with pH-triggered coating solutions of 30 wt. % cellulose acetate 398-10 (Eastman Chemical Products, Inc.) and 70 wt. % cellulose acetate phthalate CD-910 (FMC Corp.) dissolved in acetone as described in Example 1.

Figure 19:
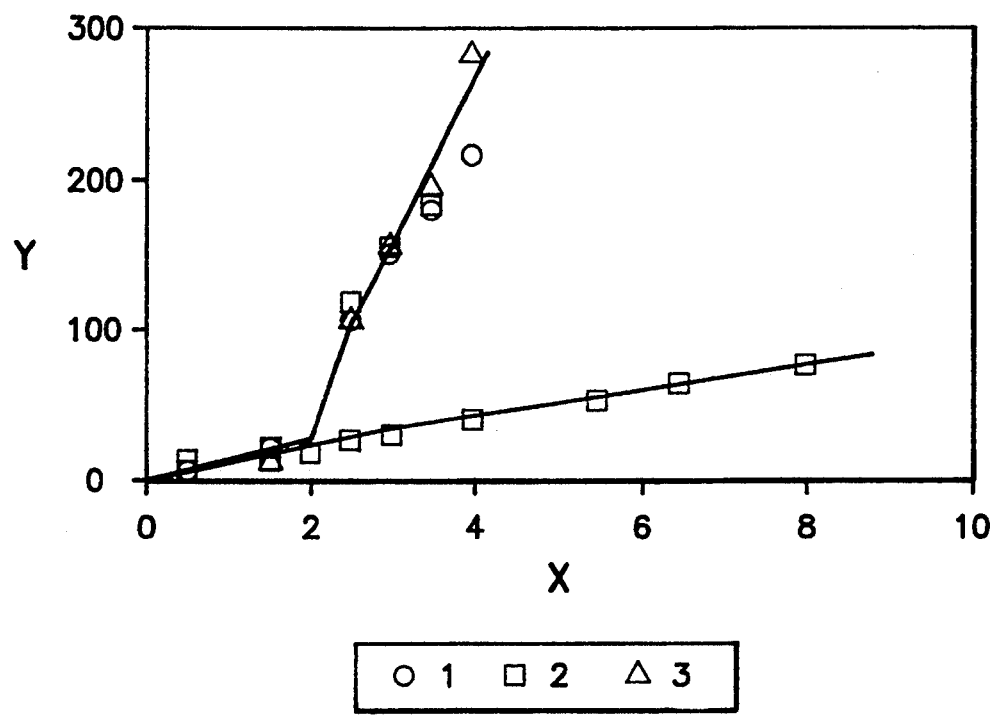
FIG. 19 is a graph of water-weight gain vs. time for tablets coated with 30/70 CNCAP tested in pH 1.2 gastric buffer transferred to intestinal buffer.

Pseudoephedrine tablets were placed in gastric buffer for two hours then a portion of the tablets were transferred to intestinal buffer (the buffer solutions are described in Example 6). Additional tablets were left in the gastric buffer for the entire test. Water weight gain of the tablets was monitored over time to obtain relative membrane permeability. The tablets left in gastric buffer had a water permeability 7 times less than that of the tablets transferred to intestinal buffer, and did not begin releasing pseudoephedrine until about 23 hours after the entire drug load was released in intestinal buffer (i.e., after approximately 29 hours in gastric buffer). The water inhibition rates in gastric and intestinal buffer can be seen in FIG. 19. As can be seen, the tablets in gastric buffer gain water at a slow constant rate whereas the tablets transferred to intestinal buffer immediately begin to gain water weight much faster. The tablets in intestinal buffer burst open after 2 hours in intestinal buffer dumping all the drug at once, while the tablets in gastric buffer did not release any drug until after about 29 hours and then only began to leak drug slowly. FIG. 19 graphs water weight gain in mgs (Y) against time in hours (X) for the six repetitions denoted by the six symbols. Three of the repetitions were transferred into intestinal buffer at two hours; these repetitions show a significant increase in slope in FIG. 19.

Both the tablets in gastric buffer and intestinal buffer begin releasing drug after the same amount of water was imbibed, but the release mechanism was entirely different. The tablets which had degraded due to the pH of the intestinal buffer burst, whereas the tablets whose coating was unaffected just leaked. This is because the burst time and bursting mechanism are determined by both the change in permeability and the change in coating strength due to degradation of the pH-sensitive polymer in the coating.

Example 21 demonstrates that the timing mechanism for pH-triggered membrane tablet coatings is due to the change in permeability of the membrane caused by a change in the pH of the receptor solution and/or due to weakening of the coating. This is evident since the tablets in intestinal buffer burst, whereas the tablets in gastric buffer barely leaked after imbibing 250 to 300 mg water/tablet.

EXAMPLE 22

DEMONSTRATION OF THE ADVANTAGE OF pH-TRIGGERED MEMBRANE COATING OVER CONVENTIONAL ENTERIC COATINGS TO CONTROL BURST

TIME AFTER A CHANGE IN THE pH OF RECEPTOR SOLUTION

Pseudoephedrine tablets made by standard direct-compression techniques and coated with a CA 398-3 semipermeable coating were coated with two different pH-triggered coating solutions. Two different coating solutions were prepared: one with 30 wt. % cellulose acetate 398-10 (Eastman Chemical Products, Inc.) and 70 wt. % cellulose acetate phthalate CD-910 (FMC Corp.), and the other with 5 wt. % cellulose acetate 398-10 (Eastman Chemical Products, Inc.) and 95 wt. % cellulose acetate phthalate CD-910 (FMC Corp.). Both were dissolved in acetone, and the tablets were coated as described in Example 1.

Figure 20:
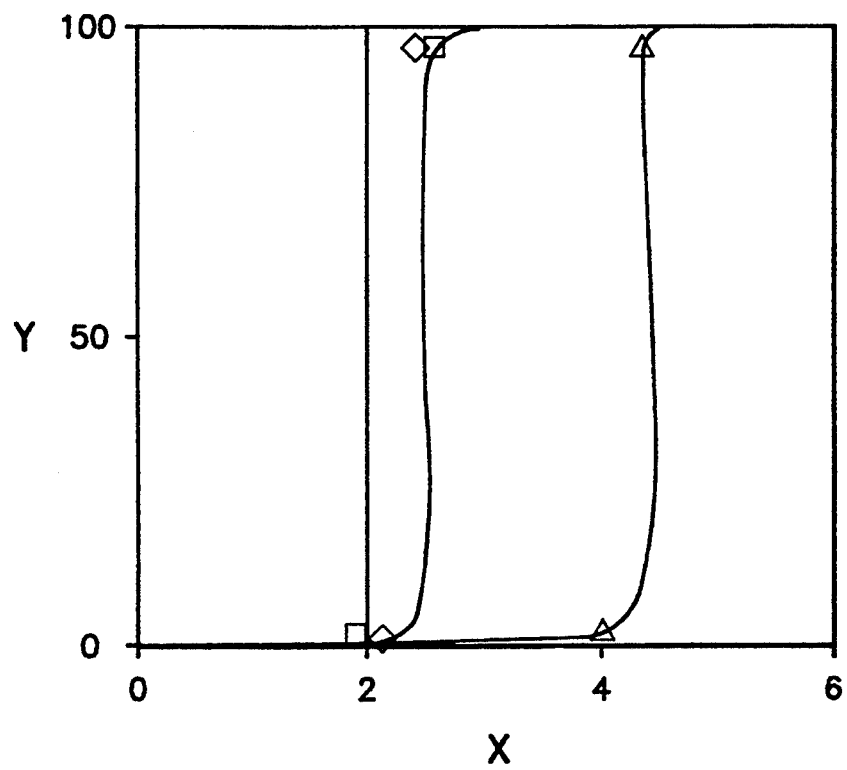
FIG. 20 is a graph of percentage of drug release vs. time for conventional enteric-coated aspirin and for two formulations of pH-triggered membrane coated pseudoephedrine tablets.

Release-rate tests were conducted as described in Example 8 to determine tablet burst times. Release-rate tests were also run on the conventional enteric-coated aspirin, Ecotrin. Visual break times were observed for the Ecotrin at less than 0.5 hour after being transferred to the intestinal buffer. The Ecotrin tablet completely disintegrated, so complete drug release was assumed. The 5/95 CA 398-10/CAP pH-triggered membrane coated tablet burst approximately 2 hours after being transferred to the intestinal buffer. The 30/70 CA 398-10/CAP pH-triggered membrane coated tablet burst approximately 2 hours after being transferred to the intestinal buffer, demonstrating the ability to target a delivery site in the intestines with the pH-triggered membrane coated tablets (FIG. 20). FIG. 20 graphs % of total drug released (Y) against time in hours (X) for the three tablets as follows: diamond-Ecotrin; square-5/95; CA 398-10/CAP, and triangle-30/70; CA 398-10/CAP.

EXAMPLE 23

DEMONSTRATION THAT A pH-TRIGGERED MEMBRANE COATING IS MORE ROBUST IN GASTRIC BUFFER SOLUTIONS (WITH A pH AS HIGH AS 6) THAN CONVENTIONAL ENTERIC COATINGS

Pseudoephedrine tablets made by standard direct-compression techniques and coated with a CA 398-3 semipermeable coating were coated with a pH-triggered coating solution of 30 wt. % cellulose acetate 398-10 (Eastman Chemical Products, Inc.) and 70 wt. % cellulose acetate phthalate CD-910 (FMC Corp.) dissolved in acetone as described in Example 1.

Release-rate tests were conducted in a potassium phosphate and sodium hydroxide buffer having a pH of 6.0 and osmotic pressure of 7 atm with continuous stirring. The tablets tested were the pH-triggered membrane coated tablets described above, and conventional enteric-coated aspirin (Ecotrin). Visual break times were observed for the tablets tested. The Ecotrin tablets disintegrated within 30 minutes, whereas all of the pH-triggered membrane coated tablets were intact after 2 hours.

Example 23 demonstrates that the pH-triggered membrane coatings are more reliable under conditions of high pH in the stomach. This demonstrates that the trigger-pH for the coating described in this example is greater than 6 and less than 7.5.

We claim:

1. An osmotic bursting device for dispensing a beneficial agent to an aqueous environment comprising:
   a. a pharmaceutical or veterinary agent;
   b. an osmagent;
   c. a wall surrounding said agent and osmagent, said wall formed at least in part of a semipermeable membrane which is permeable to the aqueous environment and substantially impermeable to the beneficial agent and osmagent; and
   d. pH-sensitive trigger means for triggering the bursting of the device and rapid release of beneficial agent as a bolus, said trigger means attached to said semipermeable membrane and said trigger means activated by a predetermined pH of from 3 to 9 wherein said device includes an aqueous swellable material and wherein said device is a capsule, said capsule formed from capsule parts, said capsule parts bonded together with said pH-sensitive trigger.

2. The device as recited in claim 1 wherein said capsule parts comprise said semipermeable membrane and wherein said semipermeable membrane is cellulose esters, cellulose ethers, polyacrylic acid derivatives, polyvinyl alcohols or polyalkenes.

3. The device as recited in claim 2 wherein said semipermeable membrane is ethylene vinyl alcohol copolymer, cellulose acetate or ethyl cellulose.

4. The device as recited in claim 2 wherein said pH-sensitive trigger means is phthalate derivatives, acrylic acid and acrylic ester copolymers, vinyl acetate and crotonic acid copolymers or shellac.

5. The device as recited in claim 4 wherein said swellable material is cellulose esters, cellulose ethers, polyacrylic acid derivatives, ethylene oxides, water-soluble gums or starches.

6. The device as recited in claim 5 wherein said swellable material is sodium carboxymethylcellulose.

7. The device as recited in claim 2 wherein said pH-sensitive trigger means comprises a mixture comprising a polymer selected from the group consisting of cellulose esters, cellulose ethers, polyacrylic acid derivatives, polyvinyl alcohols, and polyalkenes and a polymer selected from the group consisting of phthalate derivatives, acrylic acid and acrylic ester copolymers, vinyl acetate and crotonic acid copolymers and shellac.

8. The device as recited in claim 2 wherein said pH-sensitive trigger means is 5 to 50 wt. % polymethyl methacrylate and 50 to 95 wt. % acrylic acid/acrylic ester copolymer.

9. A method for the controlled delivery of a beneficial agent to an aqueous environment of use which comprises placing the device of claim 1 into the aqueous environment of use.

10. The device as recited in claim 1 which excludes a passageway through which the beneficial agent may pass and wherein said bursting is delayed such that said bursting occurs from one to six hours after said pH-sensitive trigger means is triggered.

11. An osmotic bursting device for dispensing a beneficial agent to an aqueous environment comprising:
   a. a pharmaceutical or veterinary osmotic agent;
   b. a wall surrounding said agent, said wall formed at least in part of a semipermeable membrane which is permeable to the aqueous environment and substantially impermeable to the beneficial agent; and
   c. pH-sensitive trigger means for triggering the bursting of the device and rapid release of beneficial agent as a bolus, said trigger means attached to said semipermeable membrane and said trigger means activated by a predetermined pH of from 3 to 9 wherein said device includes an aqueous swellable material and wherein said device is a capsule, said capsule formed from capsule parts, said capsule parts bonded together with said pH-sensitive trigger.

12. A method for the controlled delivery of a beneficial agent to an aqueous environment of use which comprises placing the device of claim 11 into the aqueous environment of use.

13. An osmotic device for dispensing a beneficial agent to an aqueous environment comprising:
   a. an osmotic beneficial agent;
   b. a wall surrounding said beneficial agent, said wall formed at least in part of a semipermeable membrane which is permeable to the aqueous environment and substantially impermeable to the beneficial agent; and
   d. pH-sensitive trigger means for triggering the bursting of the device and rapid release of beneficial agent as a bolus, said trigger means attached to said semipermeable membrane and said trigger means activated by a predetermined pH of from 3 to 9 wherein said device excludes a passageway through which the beneficial agent may pass and wherein said bursting is delayed such that said bursting occurs from one to six hours after said pH-sensitive trigger means is triggered.

14. An osmotic device for dispensing a beneficial agent to an aqueous environment comprising:
   a. a beneficial agent;
   b. an osmagent;
   c. a wall surrounding said beneficial agent and osmagent, said wall formed at least in part of a semipermeable membrane which is permeable to the aqueous environment and substantially impermeable to the beneficial agent and osmagent; and
   d. pH-sensitive trigger means for triggering the bursting of the device and rapid release of beneficial agent as a bolus, said trigger means attached to said semipermeable membrane and said trigger means activated by a predetermined pH of from 3 to 9 wherein said device excludes a passageway through which the beneficial agent may pass and wherein said bursting is delayed such that said bursting occurs from one to six hours after said pH-sensitive trigger means is triggered.

* * * * *